US008834936B2

(12) United States Patent
Beaulieu et al.

(10) Patent No.: US 8,834,936 B2
(45) Date of Patent: Sep. 16, 2014

(54) COSMETIC COMPOSITIONS COMPRISING ASTEROIDEA BODY FLUID AND METHODS OF USE THEREOF

(75) Inventors: Martin Beaulieu, Rimouski (CA); Estelle Loing, Quebec (CA); Catherine Fillion, Québec (CA); Patrice Dionne, St-Redempteur (CA); Alain Lavoie, Sainte-Foy (CA); Alain Thibodeau, St-Augustin-de-Desmaures (CA)

(73) Assignee: Innovactiv Inc., Rimouski (CA)

( * ) Notice: Subject to any disclaimer, the term of this patent is extended or adjusted under 35 U.S.C. 154(b) by 72 days.

(21) Appl. No.: 13/000,997

(22) PCT Filed: Jun. 23, 2009

(86) PCT No.: PCT/CA2009/000878
§ 371 (c)(1),
(2), (4) Date: Aug. 30, 2011

(87) PCT Pub. No.: WO2010/006412
PCT Pub. Date: Jan. 21, 2010

(65) Prior Publication Data
US 2011/0311640 A1    Dec. 22, 2011

Related U.S. Application Data

(60) Provisional application No. 61/074,700, filed on Jun. 23, 2008, provisional application No. 61/104,499, filed on Oct. 10, 2008.

(51) Int. Cl.
*A61K 35/56*    (2006.01)
*A61K 8/98*    (2006.01)
*A61Q 19/08*    (2006.01)

(52) U.S. Cl.
CPC .................... *A61Q 19/08* (2013.01); *A61K 8/987* (2013.01)
USPC .......................................... 424/537; 514/8.9

(58) Field of Classification Search
USPC .......................................... 424/537; 514/8.9
See application file for complete search history.

(56) References Cited

FOREIGN PATENT DOCUMENTS

| EP | 0073173 A1 | 3/1983 |
| EP | 1306387 A1 | 5/2003 |
| JP | 2000-007548 A | 1/2000 |
| JP | 2003-104895 A | 4/2003 |
| JP | 2003-3131313 A | 11/2003 |
| JP | 2004-189675 A | 7/2004 |
| JP | 2004-189676 A | 7/2004 |
| KR | 10-2005-0120127 | 12/2005 |

OTHER PUBLICATIONS

Legac et al., "Primitive Cytokines and Cytokine Receptors in Invertebrates: the Sea Star Asterias rubens as a model of study." (1996) Scandinavian Journal of Immunology, 44:375-380.*
Issaq et al., "Methods of fractionation, separation and profiling of proteins and peptides" (2002) Electrophoresis, 23:3048-3061.*
UniProt: Taxonomy, Species, asteria vulgaris, available at www.uniprot.org/taxonomy/7604 (last accessed Nov. 13, 2012).*
Elixirs.com: Homeopathy for Health, Product, Acne Clear, (2005), available at www.elixirs.com/products.cfm?productcode=a2 (last accessed Nov. 13, 2012).*
Namikoshi et al., "Skin Lotion" (Nov. 1, 2000), Japanese Patent Office, JP 2000-007548, detailed description, machine translation, pp. 1-6.*
Ferguson, "Nutrient Transport in Starfish. I. Properties of the Coelomic Fluid" (1964) Biological Bulletin, vol. 127: 33-53.*
"International Application Serial No. PCT/CA2009/000878, International Search Report mailed Oct. 8, 2009", 3 pgs.
"International Application Serial No. PCT/CA2009/000878, Written Opinion mailed Oct. 8, 2009", 9 pgs.
Demetris, A.. J., et al., "Small proline-rich proteins (SPRR) function as SH3 domain ligands, increase resistance to injury and are associated with epithelial-mesenchymal transition (EMT) in cholangiocytes", *Journal of Hepatology*, 48(2), (2008), 276-288.
Gupta, A., et al., "Wound healing in guinea pigs after topical application of starfish Pentaceraster reaulus extract", *Journal of Wound Care*, 17(10), (Oct. 2008), 441-444.
Kwon, M. C., "Anti-wrinkle Activity of Low Molecular Weight Peptides Derived from the Collagen isolated from *Asterias amurensis*", (w/ English Abstract), *Korean Journal of Food Science and Technology*, 39(6), (2007), 625-629, abstract only.
"International Application No. PCT/CA2009/000878, International Preliminary Report on Patentability issued Jan. 5, 2011", 10 pgs.
Peng, Yan, et al., "Polyhydroxy Steroids and Saponins from China Sea Starfish *Asterina* and Their Biological Activities", Chem. Pharm. Bull. 58(6) 856-858 (2010), (2010), 856-858.
"European Application Serial No. 09797296.2, Extended European Search Report mailed Dec. 6, 2013", 8 pgs.
"Mizon Returning Starfish Cream ingredients", CosDNA, [Online]. Retrieved from the Internet: <URL: http://www.cosdna.com/eng/cosmetic_ba0591087.html>, (Retrieved Nov. 11, 2013), 2 pgs.
Cancre, Isabelle, et al., "Heparin-binding molecules with growth factor activities in regenerating-tissues of the starfish *Asterias rubens*", Comparative Biochemistry and Physiology Part C 123, (1999), 285-292.
Gasser, P, et al., "Original semiologic standardized evaluation of stratum corneum hydration by Diagnoskin stripping sample", International Journal of Cosmetic Science 26, (2004), 117-127.
Ishida, Yuko, et al., "The Essential Involvement of Cross-Talk between IFN-? and TGF-β in the Skin Wound-Healing Process", The Journal of Immunology 172, (2004), 1848-1855.

* cited by examiner

*Primary Examiner* — Jon P Weber
*Assistant Examiner* — Teresa E Knight
(74) *Attorney, Agent, or Firm* — Schwegman Lundberg & Woessner, P.A.

(57) ABSTRACT

A skin care composition comprising an isolated Asteroidea body fluid or extract thereof is described. Uses and methods of use of the composition for the prevention and/or treatment of a skin disorder or condition, such as skin-aging signs, are also described.

20 Claims, 14 Drawing Sheets

A. Untreated explant

B. Explant treated with Retin-OX+™ from ROC

C. Explant treated with unfractionated body fluid

D. Explant treated with body fluid >50kDa Fraction

E. Explant treated with body fluid 5-50kDa Fraction

F. Explant treated with body fluid <5kDa Fraction

G. Relative increase in Collagen IV expression

D0 Coelomic liquid 0.5% (<0.22μm) - 3D modelization

D28 Coelomic liquid 0.5% (<0.22μm) - 3D modelization

D0 Placebo – 3D modelization

D28 Placebo – 3D modelization

COSMETIC COMPOSITIONS COMPRISING ASTEROIDEA BODY FLUID AND METHODS OF USE THEREOF

CROSS REFERENCE TO RELATED APPLICATIONS

This application is a National Entry Application of PCT application no PCT/CA2009/000878 filed on Jun. 23, 2009 and published in English under PCT Article 21(2), which itself claims priority on U.S. provisional application Ser. No. 61/074,700, filed on Jun. 23, 2008 and on U.S. provisional application Ser. No. 61/104,499, filed on Oct. 10, 2008. All documents above are incorporated herein in their entirety by reference.

STATEMENT REGARDING FEDERALLY SPONSORED RESEARCH OR DEVELOPMENT

N/A.

FIELD OF THE INVENTION

The present invention generally relates to cosmetic compositions and methods of use thereof. The present invention also relates to the prevention and/or treatment of skin conditions and disorders, such as skin-aging signs.

BACKGROUND OF THE INVENTION

Skin is a physical barrier to the environment. Alteration of the barrier properties and actual damage to this barrier cause skin aging signs and various other skin conditions and disorders.

The epidermis and the dermis, separated by the basal membrane, constitute the cutaneous covering on the hypoderm. The epidermis is the most superficial layer of the skin and provides its resistance and impermeability. Alteration of this layer will affect negatively the appearance of the skin.

Aging of the skin is a complex biological process which is mediated by a combination of the effects of time (intrinsic aging) and environmental factors (extrinsic aging) on cellular and extracellular infrastructure.

As a result of skin aging, deep changes happen at both dermis and epidermis levels. The amount of water held by the epidermis decreases, skin keratinocytes renewal rate slows down, glycosaminoglycans (GAGs) production decreases, renewal of collagen fibers diminishes and the extracellular matrix becomes disorganized. All those events conduct to the typical apparition of wrinkles and fine lines, thinning of the skin, and loss of firmness, elasticity and moisture.

Over time, dead skin cells do not shed as quickly and turnover of new skin cells may decrease slightly. The skin cells in the bottom layer of the epidermis (stratum basal) constantly multiply through cell division, forming new keratinocytes. This regenerative process is called skin cell renewal. As we age, the rate of skin cell renewal decreases, causing cells to become stickier and to not shed as easily. As a result of cell renewal decreasing, the skin becomes thinner and more susceptible to environmental damages. Eventually, the skin appears dull and rough in texture.

With age, the synthesis of GAGs decreases, affecting moisture level in the dermis, collagen synthesis and cellular proliferation. Glycosaminoglycans are associated with proteins to form proteoglycans molecules. In the dermis, proteoglycans interact with collagen fibers allowing their optimal orientation, good stability of the dermis structure and skin firmness.

Within the skin, the structural protein called collagen, found in the dermis, provides a mesh-like framework of support and strength for the skin. As we age, collagen production decreases and collagen fibers degrade at a faster rate than in earlier years. This results in an overall decrease in the amount of collagen in the dermis. Areas with less support begin to cave in and wrinkles begin to form. Thus, collagen becomes less soluble, thinner, and sparser in intrinsically aged skin. The ratio of type III to type I collagen is reported to increase with age. Histologically, young collagen is randomly organized into a meshwork of loosely interwoven bundles. Age leads to a loosening within these bundles and straightening of collagen fibers, increasing the skin's tensile strength. Elastin is a long-lived protein in human skin; it appears to accumulate damage with age and sun exposure. New elastin is synthesized in greater quantities in aged skin, but it is thought that this synthesis results in abnormally structured elastin. Also, elastin degradation does not appear to keep pace with new synthesis in aged skin. This results in massive accumulations of elastoic material, especially in photoaged skin. The abnormal structure of this elastin prevents it from functioning as it does in young skin.

Studies of primary and tertiary skin protein structures in aged skin reveal an environment unfriendly to water, with an overall increase in hydrophobic amino acids and greater folding such that aliphatic residues are more concealed from water. Also, although total amounts of GAGs appear to be increased in aged skin, these are abnormally localized on the elastoic material in the superficial dermis; thus, they are unable to bind water as well as if they were scattered appropriately throughout the unfractionated dermis. Hence, it is not surprising that, although aged skin contains increased amounts of water, most of this water is bound to itself in tetrahedral form, rather than being bound to proteins and GAGs as it is in young skin. These factors together likely contribute to increased xerosis and withered appearance of aged skin. While it tends to be an accepted assumption that lipid content decreases with age, quantitative studies are conflicting. Some indicate a marked age-related decrease in skin lipids, at least up to age 50 years, while others indicate little or no relationship.

Cutaneous tissue repair aims at restoring the barrier function of the skin. To achieve this, defects need to be replaced by granulation tissue to form new connective tissue, and epithelial wound closure is required to restore the physical barrier. Different wound-healing phases are recognized, starting with an inflammation dominated early phase giving way to granulation tissue build-up and scar remodeling after epithelial wound closure has been achieved. In the granulation tissue, mesenchymal cells are maximally activated; cells proliferate, and synthesize huge amounts of extracellular matrix. Epithelial cells also proliferate and migrate over the provisional matrix of the underlying granulation tissue, eventually closing the defect. There is ample evidence that keratinocytes stimulate fibroblasts to synthesize growth factors, which in turn will stimulate keratinocyte proliferation in a double paracrine manner. Moreover, fibroblasts can acquire a myofibroblast phenotype under the control of keratinocytes. This depends on a finely tuned balance between a proinflammatory or a transforming growth factor (TGF)-β-dominated environment. As the phenotype of fibroblasts from different tissues or body sites becomes better defined, we may understand their individual contribution in wound healing in more detail and possibly explain different clinical outcomes.

To date, the best known way to solve these age-related problems is retinol. Retinol belongs to the retinoids family, a class of chemical compounds that are related chemically to vitamin A. Retinol is easily absorbed by the epidermis and is known to have a broad spectrum of biological activities. More specifically, retinol increases cellular renewal in the basal layer of the epidermis, normalizes cellular differentiation and regulates the keratinization process. It also has an effect on the dermis. Studies on humans have shown that retinol increase the quantity of collagen in the dermis. It also has been shown to increase skin elasticity and to reduce the depth of wrinkles on women. Presently, retinol represents the most effective non-surgical treatment approach on the market for counteracting skin aging and wrinkles. Topical retinoids have been proven to prevent and repair clinical features of photo-aging; these processes are facilitated by an ability to prevent loss of collagen from, and stimulate new collagen formation in, the papillary dermis of sun-exposed skin. Emerging evidence indicates that intrinsic, chronological aging of the skin shares several mechanistic features with photoaging. Indeed aged skin is characterized by retinoid sensitivity and is probably reparable by application of topical retinoids.

Despite their numerous benefits, the utility of topical retinol as a treatment for improving the appearance of aged and photodamaged skin, is limited by erythema, scaling/dryness, burning/stinging and irritation that occurs during the early phases and long term use of facial retinization. These concerns are often leading to the withdrawal and failure of the retinol-associated treatment.

Therefore, there remains a need to develop new approaches for the prevention and/or treatment of skin-aging signs and other skin conditions and disorders such as scar healing.

The present description refers to a number of documents, the content of which is herein incorporated by reference in their entirety.

SUMMARY OF THE INVENTION

The present inventors have surprisingly discovered that Asteroidea's body fluid has many physiologic effects on skin without cytotoxic side effects.

More specifically, in accordance with an aspect of the present invention, there is provided a skin care composition comprising an isolated Asteroidea body fluid or extract thereof.

In a specific embodiment, the skin care composition further comprises a topically acceptable carrier. In another embodiment, the Asteroidea is *Asteria vulgaris*. In another embodiment, the skin care composition is for preventing or reducing a skin condition or disorder in a subject. In another embodiment, the skin condition or disorder is a skin aging sign. In another embodiment, the condition or disorder is a scar or a stretchmark. In another embodiment, the Asteroidea body fluid or extract thereof is substantially free of molecules having a molecular weight below about 50 kDa. In another embodiment, the Asteroidea body fluid or extract thereof is substantially free of molecules having a molecular weight above about 5 kDa. In another embodiment, the Asteroidea body fluid or extract thereof is substantially free of molecules having a molecular weight above about 50 kDa and below about 5 kDa. In another embodiment, the Asteroidea body fluid or extract thereof comprises TGF-β1. In another embodiment, the Asteroidea body fluid or extract thereof is present at a concentration between about 0.01% to about 5% w/w of the composition. In another embodiment, wherein the Asteroidea body fluid or extract thereof comprises TGF-β1.

In accordance with another aspect of the present invention, there is provided a method for preventing or reducing a skin aging sign or a skin condition or disorder in a subject, comprising administering a composition comprising an effective amount of an isolated Asteroidea body fluid or extract thereof on the subject's skin.

In a specific embodiment of the method, the administration results in one or more of: (a) stimulation of the expression of a gene involved in cellular migration; (b) improved epidermis cell migration; (c) increased collagen fibers thickness; (d) increased number of collagen fibers; (d) reduced keratination of stratum corneum; (e) increased keratinocyte proliferation; (f) increased keratinocyte terminal differentiation; (g) increased epidermis thickness; (h) increased glycosaminoglycans (GAGs) expression; (i) increased density of mitotic cell in epidermis; (j) increased number of epidermis cellular layers; (k) increased expression of at least one of collagen III, collagen IV and collagen VII; (l) reduced crow's feet depth; (m) reduced mouth wrinkles; (n) increased skin firmness; and (o) increased skin moisture.

In another specific embodiment of the method, the one or more gene(s) involved in cellular migration is a small proline-rich protein gene. In another specific embodiment of the method, the small proline-rich protein is SPRR2A. In another specific embodiment of the method, the administration results in an increased expression of at least one of collagen III, collagen IV and collagen VII. In another specific embodiment of the method, an Asteroidea body fluid or extract thereof is substantially free of molecules having a molecular weight below 50 kDa. In another specific embodiment of the method, the Asteroidea body fluid or extract thereof is substantially free of molecules having a molecular weight above 5 kDa. In another specific embodiment of the method, the Asteroidea body fluid or extract thereof is substantially free of molecules having a molecular weight above 50 kDa and below 5 kDa. In another specific embodiment of the method, the Asteroidea body fluid or extract thereof comprises TGF-β1. In another embodiment of the method, the administered composition comprises an Asteroidea body fluid or extract thereof present at a concentration between about 0.01% to about 5% w/w of the composition.

In accordance with another aspect of the present invention, there is provided a use of an isolated Asteroidea body fluid or extract thereof for the manufacture of a skin care composition.

In accordance with another aspect of the present invention, there is provided a use of an isolated Asteroidea body fluid or extract thereof for preventing or reducing a skin aging sign in a subject.

In a specific embodiment of the use, the use results in one or more of: (a) stimulation of the expression of a gene involved in cellular migration; (b) improved epidermis cell migration; (c) increased collagen fibers thickness; (d) increased number of collagen fibers; (d) reduced keratination of stratum corneum; (e) increased keratinocyte proliferation; (f) increased keratinocyte terminal differentiation; (g) increased epidermis thickness; (h) increased glycosaminoglycans (GAGs) expression; (i) increased density of mitotic cell in epidermis; (j) increased number of epidermis cellular layers; (k) increased expression of at least one of collagen III, collagen IV and collagen VII; (l) reduced crow's feet depth; (m) reduced mouth wrinkles; (n) increased skin firmness; and (o) increased skin moisture.

In another specific embodiment of the use, the one or more gene(s) involved in cellular migration is a small proline-rich protein gene. In another specific embodiment of the use, the small proline-rich protein is SPRR2A. In another specific embodiment of the use, the use results in an increased expression of at least one of collagen III, collagen IV and collagen VII. In another specific embodiment of the use, the Asteroidea body fluid or extract thereof is substantially free of molecules having a molecular weight below 50 kDa. In another specific embodiment of the use, the Asteroidea body fluid or extract thereof is substantially free of molecules having a molecular weight above 5 kDa. In another specific embodiment of the use, the Asteroidea body fluid or extract thereof is substantially free of molecules having a molecular weight above 50 kDa and below 5 kDa. In another specific embodiment of the use, the Asteroidea body fluid or extract thereof comprises TGF-β1. In another specific embodiment of the use, the Asteroidea body fluid or extract thereof is used at a concentration between about 0.01% to about 5% w/w of the composition.

Other objects, advantages and features of the present invention will become more apparent upon reading of the following non-restrictive description of specific embodiments thereof, given by way of example only with reference to the accompanying drawings.

DETAILED DESCRIPTION OF ILLUSTRATIVE EMBODIMENTS

Figure 1:
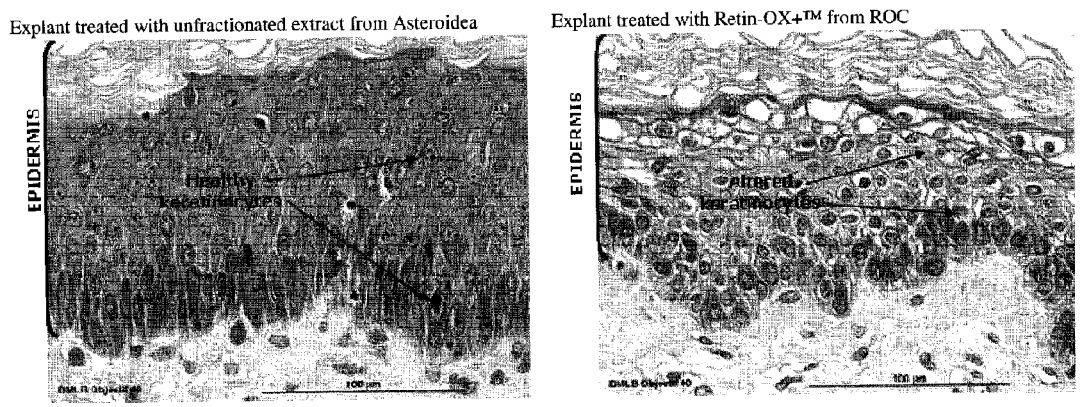
FIG. 1 presents photographs of skin explants treated with unfractionated Asteroidea body fluid extract (left panel) and with Retin-OX+™ (right panel)

Echinoderms (including Asteroidea (starfishes)) are unique among major groups of animals in that they have no recognizable excretory organs to assist them in maintaining fluid and osmotic balance, and they do not possess impervious integuments to protect them from the external environment. Unlike many other forms, they presumably do not drink and excrete water or ions to maintain fluid homeostasis. Most sources describe them as being simply 'isosmotic' and remain silent on the issue of how they regulate fluid volume. This lack of interest is especially surprising considering that echinoderms are completely dependent on hydraulic mechanisms to drive their appendages, and a number of species are soft-bodied, relying partially on internal turgor to support their shape or at least to inflate their respiratory papulae. Clearly, even in stable environments, most echinoderms face continual losses of fluid that must be balanced.

The means by which starfish transport nutrient materials from absorptive sites, in the digestive glands to the various other tissues has been the subject of much uncertainty. At least five distinct mechanisms have been proposed by which this might be accomplished. These are: (1) circulation through the perivisceral coelom; (2) transport via the coelomocytes; (3) movement through the haemal channels; (4) circulation through the perihaemal space; and (5) circulation through the water vascular system. Little evidence appears to support any of these theories, and arguments may be directed against each of them. The most obvious route for nutrient transport is through the perivisceral coelom. This is a spacious cavity, whose fluid may account for as much as 25% of the body weight. It contains or lies adjacent to most of the important structures of the body.

The present inventors have shown that the effects of purified Asteroidea body fluid towards both dermal and epidermal cells is similar to that of retinol (e.g., Retin-OX+™ from ROC), but without the cytotoxic effects associated with retinol. The effects of the purified Asteroidea body fluid include for example the renewal of the epidermis by regulating keratinocytes proliferation and differentiation. It also protects and repairs the dermis by stimulating the synthesis of GAGs and collagens.

The body fluid may be obtained from any echinoderm belonging to the class Asteroidea. As used herein the term "Asteroidea" refers to any orders of this class including but not limited to Brisingida, Forcipulatida, Notomyotida, Paxillosida, Peripoda, Platyasterida, Spinulosida, Valvatida, Velatida. In specific embodiment, it refers to families of the Forcipulatida order including Asteriidae, Heliasteridae and Zoroasteridae. In more specific embodiments it refers to genera of the Asteriidae family including the *Ampheraster, Anteliaster, Aphanasterias, Asterias* such as *Asteria vulgaris* and *Asteria forbesii, Astrometis, Coronaster, Coscinasterias, Evasterias, Leptasterias* such as *Leptasterias polaris* and *Leptasterias hexactis, Lethasterias, Marthasterias, Orthasterias, Pedicellaster, Pisaster* such as *Pisaster ochraceus* and *Pisaster giganteus, Pycnopodia, Rathbumaster, Sclerasterias, Stenasterias, Stephanasterias, Stichastrella, Stylasterias, Tarsaster* and *Urasterias*. In a specific embodiment, it refers to suborders of the Spinulosida order including Eugnathina and Leptognathina. In specific embodiment, it refers to families of the Eugnathina suborder including Korethrasteridae, Pterasteridae, Pythonasteridae and Solasteridae including the genera *Crossaster* such as *Crossaster papossus, Heterozonias, Lophaster* and *Solaster*. In specific embodiment, it refers to families of the Leptognathina suborder including Acanthasteridae, Asterinidae such as *Asterina Miniata*, Echinasteridae, Henricia, Ganeriidae, Metrodiridae, Mithrodiidae, Poramidae and Valvasteridae. It also includes *Linkia* such as *Linkia Gildingi*, and *Choriaster* such as *Choriaster granulatus* Sweet. Other members of the Asteroidea class are also listed in Elizabeth (2005-11-22). Asterozoa: Fossil groups: SciComms 05-06: Earth Sciences. The present invention also encompasses the use of Ophiuroidea coelomic fluid. It includes native and recombinant Asteroidea.

As used herein, the term "isolated" in the expressions "isolated Asteroidea body fluid" or "isolated Asteroidea body fluid extract" means altered "by the hand of man" from its natural state (i.e. if it occurs in nature, it has been removed from its original environment). For example, an Asteroidea body fluid naturally present in an Asteoida is not "isolated", but the same Asteroidea body fluid separated from the coexisting materials of its natural state (e.g., shell) is "isolated" as this term is employed herein.

As used herein, the term "extract" in the expression "Asteroida body fluid extract" refers to a fraction of an Asteroida body fluid. Without being so limited, an Asteroidea body fluid from which bacteria and/or coelomocyte have been separated is a type of Asteroidea body fluid extract. An Asteroida body fluid from which water has been substantially removed (e.g., lyophilized) is an other type of Asteroidea body fluid extract. A active fraction of Asteroida body fluid consisting of the filtrate or the concentrate of a filtration with a specific membrane (e.g., active filtrate of retentate of 0.22 micrometer membrane, of 5 kDa cut-off membrane, of 10 kDa cut-off membrane, 15 kDa cut-off membrane, 20 kDa cut-off membrane, 25 kDa cut-off membrane, 30 kDa cut-off membrane, 35 kDa cut-off membrane, 40 kDa cut-off membrane, of 50 kDa cut-off membrane, of 60 kDa cut-off membrane, of 70 kDa cut-off membrane, of 80 kDa cut-off membrane) is also an extract. The active acidic, basic or neutral fraction of the fluid which may be isolated by charge separation methods (e.g., purification by liquid-phase isoelectric focusing (IEF) using a Rotofor Purification System™ by Biorad) is also an extract. An active (i.e. displaying an anti-aging property) portion of the fluid resulting from any method of fractionation consisting of at least 5%, 10%, 15%, 20%, 25%, 30%, 65%, 70%, 75%, 80%, 85%, 90%, 95%, 96%, 97%, 98%, 99% (% v/v or w/w) of the isolated Asteroidea body fluid is also an extract. A single molecule isolated from the Asteroidea body fluid is not an extract with the meaning of the present application.

Accordingly, in a first aspect, the present invention provides a skin care composition comprising an Asteroidea or Ophiuroidea body fluid extract.

In an embodiment, the body fluid extract is obtained from the coelom of the Asteroidea (i.e. coelomic fluid extract). In an embodiment, the body fluid extract may be filtered or fractionated using molecular sieving or specific fractionation techniques well known in the art. The extract may also be further concentrated or diluted. It can also be lyophilized or otherwise treated to increase at least one of its skin care properties.

In an embodiment, the extract is substantially free of molecules having a molecular weight below 50 kDa (>50 kDa fraction). Such an extract may be obtained, for example, by collecting the retentate fraction following filtration of the above-mentioned body fluid extract on a filter having a cutoff of 50 kDa. Other separations means such as electrodialysis or electrofractionating can be used. "Substantially free" used herein is meant to reflect the inherent imprecision of filtration membranes or other separation equipments.

In an embodiment, the extract is substantially free of molecules having a molecular weight above 5 kDa (<5 kDa fraction). Such an extract may be obtained, for example, by collecting the filtrate fraction following filtration of the above-mentioned body fluid extract on a filter having a cutoff of 5 kDa.

In another embodiment, the extract is substantially free of molecules having a molecular weight above 50 kDa and below 5 kDa (5-50 kDa fraction). Such an extract may be obtained, for example, by collecting the filtrate fraction following filtration of the above-mentioned body fluid extract on a filter having a cutoff of 50 kDa, and submitting this filtrate fraction to a second filtration on a filter having a cutoff of 5 kDa, and collecting the retentate fraction.

The composition of the present invention may be formulated in a topically applicable pharmaceutical or cosmetic composition (e.g., a topical formulation). Carriers included in topically applicable compositions of the present invention are topically acceptable carriers. Non-limitative examples of such topically applicable compositions include skin care cream, cleansing cream, ointment, skin care lotion, skin care gel, skin care foam, sun care composition, make-up removal cream, make-up removal lotion, foundation cream, liquid foundation, bath and shower preparation, deodorant composition, antiperspirant composition, shaving products composition, after-shave gel or lotion, beauty aids composition, depilatory cream, soap composition, hand cleaner composition, cleansing bar, baby care, hair care, shampoo, setting lotion, treatment lotion, hair cream, hair gel, coloring composition, restructuring composition, permanent composition, anti-hair loss composition, or any other composition which is adapted for the use in a topical cosmetic regimen.

Creams, as is well known in the art of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a non-ionic, anionic, cationic or amphoteric surfactant.

Lotions are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other cosmeceutically acceptable chemicals to buffer, stabilize or preserve the solute. Common examples of solvents used in preparing solutions are ethanol, water, propylene glycol or any other cosmeceutically acceptable vehicles.

Gels are semisolid, suspension-type systems. Single-phase gels contain organic macromolecules distributed substantially uniformly throughout the carrier liquid, which is typically aqueous, but also, preferably contain an alcohol, and, optionally, an oil. "Organic macromolecules," i.e. gelling agents, are cross linked acrylic acid polymers such as the "carbomer" family of polymers, e.g., carboxypolyalkylenes that may be obtained commercially under Carbopol™. The carbomer formulation described in certain Examples herein is a gel. Other examples are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stiffing, or combinations thereof.

Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399-1404, and ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the anti-aging formulations. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin™ (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

In an embodiment, the composition of the present invention may further comprise at least one additional active agent, such an agent that modulates cell differentiation or proliferation, an anesthesic agent, anti-acne agent, anti-aging agent, antibacterial agent, anticellulite agent, antifungal agent, anti-inflammatory agent, anti-irritant agent, antioxidant agent, antiparasitic agent, antipollution agent, antipruritic agent, anti-rosacea agent, anti-seborrhea agent, anti-stress agent, anti-telangiectasia agent, antiviral agent, anti-wrinkle agent, baby care agent, bath and body agent, calming agent, cleansing agent, collagen synthesis agent, elastase inhibitory agent, exfoliant agent, facial peeling agent, firming agent, foot care agent, free radical scavenging agent, immune function modulator agent, keratolytic agent, lift agent, make-up remover agent, melanogenesis stimulator agent, hair care agent, matrix metalloproteinase inhibitory agent, moisturizing agent, oil absorbent agent, osmoregulator agent, anti-photoaging agent, protecting agent, rejuvenating agent, regenerating agent, restructuring agent, sensitive skin agent, shaving product agent, skin defense enhancer agent, skin clarifier agent, skin repair agent, slimming agent, smoothing agent, softening agent, soothing agent, sun care agent, sunless tanning agent, tensing agents and whitening agent, or any other agent adapted for use in a cosmetic regimen that comprises topical application of the cosmetic composition, and which complements or supplements the effect of the body fluid extract composition of the present invention. In a further embodiment, the above-mentioned at least one additional active ingredient modulate(s) at least one of cell differentiation, cell metabolic activity, cell structure, cell proliferation, extracellular processes and pigmentation.

Without being so limited, agents that modulate cell differentiation or proliferation include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin D and its derivatives (cholecalciferol, ergocalciferol, 25-hydroxycholecalciferol), growth factors, estradiol derivatives. It also includes any combination thereof.

Without being so limited, anaesthesics include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include lidocaine chlorhydrate and its derivatives. It also includes any combination thereof.

Without being so limited anti-acne agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include benzoyl peroxide, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), salicylic acid, sulfur, sulfurated lime, alcohol and acetone. It also includes any combination thereof.

Without being so limited, anti-aging/anti-wrinkle agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include hyaluronic acid, sodium-2-pyrrolidone carboxylate, glycosaminoglycans, kinetin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), epidermal growth factor, ceramide, ethylbisiminomethylguaiacol manganese chloride, glycation inhibitors, chrysanthellum indicum extract and aphanizomenon flos aquae extract. It also includes any combination thereof.

Without being so limited, antibacterial agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include eucalyptus extract, clindamycin phosphate, cavacrol, erythromycin and antibiotics belonging to the group of tetracyclines. It also includes any combination thereof.

Without being so limited, antifungal agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include econazole, ketoconazole, miconazole, amphotericin B, terbinafine and octopirox. It also includes any combination thereof.

Without being so limited, anti-inflammatory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, vitamin E and its derivatives (α-tocopherol, δ-tocopherol, γ-tocopherol), chamomile oil, gingko biloba oil and *camellia sinensis* extract. It also includes any combination thereof.

Without being so limited, anti-irritant/soothing/smoothing/calming agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, *camellia sinensis* extract, lavender oil, aloe vera, linden extract, epilobium angustifolium extract, chysanthellum indicum extract, cola nitida extract and alteromonas ferment extract. It also includes any combination thereof.

Without being so limited, antioxidant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include furfuryladenine, panthenol, lipoic acid, ubiquinone, niacinamide, melatonin, catalase, glutathione, superoxide dismutase, polyphenols, cysteine, allantoin, kinetin, vitamin C and its derivatives (ascorbyl palmitate, magnesium ascorbyl phosphate, sodium ascorbyl phosphate), vitamin E and its derivatives (α-tocopherol, δ-tocopherol, γ-tocopherol), grape seed extract and *camellia sinensis* extract. It also includes any combination thereof.

Without being so limited, antipruritic agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include thenaldine, trimeprazine, cyproheptadine. It also includes any combination thereof.

Without being so limited, anti-rosacea/anti-telangiectasia agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include metronidazole, vasoconstrictors, benzoyl peroxide, azelaic acid, sulphur, soy proteins and glycosaminoglycans. It also includes any combination thereof.

Without being so limited, anti-seborrhea agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include progesterone derivatives, isoleutrol and hinokitiol. It also includes any combination thereof.

Without being so limited, sensitive skin agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rose oil and jasmine oil. It also includes any combination thereof.

Without being so limited, cleansing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include ammonium lauryl sulfate, ammonium laureth sulfate, cocamide MEA, triethanolamine lauryl sulfate, sodium stearate and nettle leaf extract. It also includes any combination thereof.

Without being so limited, collagen synthesis agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin C and its derivatives (ascorbyl palmitate, magnesium ascorbyl phosphate, sodium ascorbyl phosphate), growth factors and its derivatives. It also includes any combination thereof.

Without being so limited, exfoliant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include alpha/beta hydroxy acids, salicylic acid, glycolic acid, lactic acid, citrus acid and walnut shell powder. It also includes any combination thereof.

Without being so limited, facial peeling agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include glycolic acid, lactic acid, trichloroacetic acid and phenol. It also includes any combination thereof.

Without being so limited, firming/tensing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dimethylaminoethanol, neuro-cosmetic actives (Botox™-like), chitosan, arnica extract, fennel-sweet oil and papaya extract. It also includes any combination thereof.

Without being so limited, free radical scavenging/antipollution/anti-stress agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include grape seed extract, alpha-tocopherol and the esters thereof, superoxide dismutase, some chelating agents of metals, vitamin C and its derivatives (ascorbyl palmitate, magnesium ascorbyl phosphate, sodium ascorbyl phosphate). It also includes any combination thereof.

Without being so limited, hair care agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-D-glucosamine, poly-N-acetyl-D-glucosamine, stearalkonium chloride and triethanolamine lauryl sulfate. It also includes any combination thereof.

Without being so limited, matrix metalloproteinase inhibitory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *camellia sinensis* extract, polyphenols, spatholobi caulis extract, euonymus alatus extract, rhizoma notopterygii extract, quercetin, glycosaminoglycans, polymethoxy flavonoid, N-acetyl-cysteine, 2-furildioxime, isoflavone, vitamin C and its derivatives (ascorbyl palmitate, magnesium ascorbyl phosphate, sodium ascorbyl phosphate), retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester) and hydroxamate derivatives. It also includes any combination thereof.

Without being so limited, moisturizing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include cucumber extract, sodium-2-pyrrolidone carboxylate, sodium PCA, sodium hyaluronate, chitin and its derivatives, alpha hydroxy acids, hyaluronic acid and hydrolysed wheat protein. It also includes any combination thereof.

Without being so limited, osmoregulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include mannitol, dulcitol and betaine.

Without being so limited, protecting agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-N-acetyl-D-glucosamine, poly-D-glucosamine, alkyloamides, chitosan, chrysanthellum indicum extract, *camellia sinensis* extract and alteromonas ferment extract. It also includes any combination thereof.

Without being so limited, rejuvenating agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rosemary extract, rosewood extract, geranium extract and vitamin E and its derivatives α-tocopherol, δ-tocopherol, γ-tocopherol). It also includes any combination thereof.

Without being so limited, skin repair agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), allantoin, eucalyptus extract, lavender oil, rose oil and activators of collagen synthesis and activators of components of the skin's extracellular matrix. It also includes any combination thereof.

Without being so limited, slimming/anticellulite agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include chrysanthellum indicum extract, dihydromyricetin, theobromine, theophylline, aminophylline, caffeine, isopropylarterenol hydrochloride, epinephrine, α-MSH agonists, adenylate cyclase activators and phosphodiesterase inhibitors. It also includes any combination thereof.

Without being so limited, sun care/photo aging agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include PABA (p-aminobenzoic acid) and derivatives, gluconolactone, salicylates, cinnamates, benzophenones, dibenzoylmethanes, oxybenzone, vitamin E and its derivatives (α-tocopherol, δ-tocopherol, γ-tocopherol), ethylbisiminomethylguaiacol manganese chloride, glycosaminoglycans, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), titanium dioxide, octyl methoxycinnamate, benzophenone, octyl salicylate, epilobium angustifolium extract, *rumex occidentalis* extract, chrysanthellum indicum extract, *camellia sinensis* extract and alteromonas ferment extract. It also includes any combination thereof.

Without being so limited, sunless tanning/melanogenesis stimulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dihydroxyacetone, α-MSH agonists, adenylate cyclase activators and phosphodiesterase inhibitors. It also includes any combination thereof.

Without being so limited, toning agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include nettle extract, orange blossom extract, rosewood extract and witch hazel extract. It also includes any combination thereof.

Without being so limited, whitening/pigmentation agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include arbutin, azealeic acid, vitamin C and its derivatives (ascorbyl palmitate, magnesium ascorbyl phosphate, sodium ascorbyl phosphate), hydroquinone, N-acetyl-4-S-cysteanimylphenol, kojic acid, melanostat (melanostatine), tretinoin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), *ruminex occidentalis* extract, licorice, mulberry, arctostaphylos uva-ursi (bearberry), tyrosinase inhibitors, melanosome-transfer inhibitors and melanin scavengers. It also includes any combination thereof.

In an embodiment, the composition of the present invention further comprises a pharmaceutically acceptable topical carrier, vehicle, excipient or additives (i.e. topically/cosmetically acceptable carrier, vehicle, excipient or additives). Such carrier, vehicle, excipient or additives are well known in the art and may be used, for example, to improve final formulation regarding organoleptic properties, skin penetration and accessibility of the active ingredient. Examples of carriers, vehicles or excipients include: buffering agent, carrier agent, chelating agent, conditioner agent, coloring agent, detackifier agent, emollient agent, emulsifier agent, film former agent, foaming agent, humectant agent, lactylate agent, lipophilic agent, lubricant agent, neutralizer agent, oil agent, opacifier agent, preservative agent, solubilizer agent, solvent agent, stabilizer agent, surfactant agent, thickener agent, viscosity agent, water absorbent agent, wetting agent, perfume and thermal water. It also includes any combination thereof.

The composition of the present invention may be formulated so as to provide for a specifically controlled delivery system. Non-limitative examples of such delivery systems include slow delivery system, rapid delivery system, immediate delivery system, delayed delivery system, zero-order delivery system and dual or multiple speed delivery system. Such controlled delivery systems may be achieved with specific formulations including chemical delivery systems, multiple emulsions, microemulsions, nanoemulsions, encapsulations such as liposomes, microspheres, nanospheres, microsponges, beads and cyclodextrins, polymeric matrices, polymeric cosmetic conjugates, oil body/oleosin, oil-soluble molecular film, skin patches, unit dosages.

Without being so limited, buffering agents are salts of bases/acids, compatible with the nature of the skin and with its pH. Sodium acetate is an example of a frequently used buffer agent.

Without being so limited, carder agents are ingredients capable of aiding the application of the active ingredient. Isohexadecane is an example of a frequently used carrier.

Without being so limited, chelating agents are ingredients capable of binding mono and divalent cations, such as EDTA, trisodium EDTA, tetrasodium EDTA, disodium EDTA or a combination thereof.

Without being so limited, conditioner agents are ingredients with lubricating action and hydrating effect, such as cetrimonium chloride, dicetyldimonium chloride, trideceth-12, quaternium-Z7, quaternium-18, polyquaternium-10, behentrimonium methosulfate, cetearyl alcohol, stearamidopropyl dimethylamine, trimethylsilylamodimethicone, isolaureth-6, octoxynol-4, dimethicone, dimethiconol, cyclopentasiloxane, pareth-7, pareth-9, linoleic acid and glycerin, or a combination thereof.

Without being so limited, detackifier agents are ingredients capable of adsorbing onto tacky materials and reduce their tendency to adhere, such as cyclopentasiloxane, dimethicone and vinyl dimethicone, phenyl trimethicone, isopropyl esters, isostearate esters, dimethyl sebacate and dipropyl sebacate, or a combination thereof.

Without being so limited, emollient agents are ingredients with lubricating action and hydrating effect, such as isopropyl palmitate, sunflower seed oil, mineral oil, stearyl stearate, isopropyl myristate, lanolin, caprylic, capric triglyceride, cyclopentasiloxane, dimethicone, vinyl dimethicone, bisphenylpropyl dimethicone, alkyl dimethicone, sorbitan stearate, sucrose distearate, myristyl alcohol, myristyl lactate, cetyl acetate, dicaprylyl ether, floraester-20, maleated soybean oil, cyclomethicone, shea butter, hydrogenated coconut oil, isopropyl palmitate, diisostearoyl trimethylolpropane siloxy silicate and alkyl benzoate, or a combination thereof.

Without being so limited, emulsifier agents are ingredients capable of preventing the separation of immiscible substances in an emulsion, of helping to distribute evenly one substance in another, of improving texture, homogeneity, consistency and stability, such as cetearyl alcohol, glyceryl stearate, alkyl acrylate crosspolymer, stearic acid, emulsifying wax, sorbitan oleate, sorbitan stearate, polysorbate, polyethylene glycopolysorbate, triethanolamine, cyclopentasiloxane, dimethicone copolyol, PEG-30 dipolyhydroxystearate, sucrose distearate, PEG-100 stearate, sodium dioctylsulfosuccinate, polyacrylamide, isoparaffin, laureth-7, cetyl phosphate, DEA cetyl phosphate, glycol stearate, stearyl alcohol, cetyl alcohol, behentrimonium methosulfate and ceteareth-2, or a combination thereof.

Without being so limited, film former agents are ingredients capable of forming a dimensionally stable and continuous film to minimize the formula tackiness, such as wheat protein, eicosene copolymer, perfluoromethylisopropyl ether, diisostearoyl trimethylolpropane siloxy silicate, trimethylsiloxysilicate, dimethicone, vinyl dimethicone and cyclopentasiloxane, or a combination thereof.

Without being so limited, foaming agents are ingredients capable of regulating the amount of air in a product, such as lauramide DEA and cocamide MEA, disodium laureth sulfosuccinate, disodium N-octadecyl sulfosuccinamate, ammonium lauryl sulphate, triethanolamine lauryl sulfate, sodium lauryl sulphate and sodium 2-ethylhexylsulfate, or a combination thereof.

Without being so limited, humectant agents are ingredients capable of maintaining constant humidity and retaining moisture, such as glycerine, PEG-8, butylene glycol and propylene glycol, or a combination thereof.

Without being so limited, lubricant agents are ingredients capable of adding slipperiness and reducing friction to improve application, such as dimethicone and dimethicone copolyol, or a combination thereof.

Without being so limited, neutralizer agents are ingredients capable of changing the acid-alkaline balance, such as triethanolamine and sodium hydroxide, or a combination thereof.

Without being so limited, opacifier agents are ingredients capable of changing the look of a clear or translucent product to a creamier or pearlier one, such as glyceryl stearate and PEG-100 stearate, or a combination thereof.

Without being so limited, preservative agents are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben, or a combination thereof.

Without being so limited, solubilizer agents are ingredients capable of allowing incompatible ingredients to become part of a homogeneous solution, such as polysorbate, ceteareth, steareth and PEG, or a combination thereof.

Without being so limited, stabilizer agents are ingredients capable of maintaining physical and chemical properties during and after processing, preventing or limiting changes in the physical properties of a substance during product life, such as polyethylene, sodium chloride, stearyl alcohol, xanthan gum, tetrasodium EDTA and dimethicone copolyol, or a combination thereof.

Without being so limited, surfactant agents are ingredients capable of reducing surface tension when dissolved in water or a water solution, reducing interfacial tension between two liquids or between a liquid and a solid, such as sodium dioctylsulfosuccinate, octoxynol-40, isolaureth-6, ammonium lauryl sulfate, lauryl alcohol, lauramide DEA and cocoamidopropyl betaine, or a combination thereof.

Without being so limited, thickener agents are ingredients capable of absorbing water to impart body, improve the consistency or texture, and stabilize an emulsion, such as stearic acid, magnesium aluminum silicate, carbomer (including sodium carbomer and potassium carbomer), alkyl acrylate crosspolymer, polyacrylamide, isoparaffin, laureth-7, cetyl alcohol, xanthan gum, alkyl dimethicone, hydroxyethylcellulose, glyceryl stearate, pentaerythrityl tetrastearate, stearyl alcohol and polyquaternium-10, or a combination thereof.

Without being so limited, viscosity agents are ingredients capable of controlling the degree of fluidity and the internal resistance to flow exhibited by a fluid, such as magnesium aluminum silicate, caprylyl glycol and myristyl alcohol, or a combination thereof.

Without being so limited, water absorbent agents are ingredients capable of absorbing the product's water to maintain the moisture, such as carboxyvinyl polymer, acrylic copolymer, polyacrylamide, polysaccharides, natural gum, clay, modified clay, metallic salt, fatty acid, or a combination thereof.

Without being so limited, wetting agents are ingredients capable of reducing the surface tension of the water for better penetration or spread over the surface, such as caprylate, caprylyl glycol, glyceryl caprate, polyglyceryl-2 caprate, polyglyceryl-6, polyglyceryl-3 laurate and TEA-laureth sulfate, or a combination thereof.

The isolated Asteroidea body fluid or extract thereof or compositions of the present invention may be packaged in any suitable manner, including but not limited to, a jar, a bottle, a tube, a stick, a roller-ball applicator, an aerosol spray device, etc., in the conventional manner. The extract or compositions of the present invention could be packaged as a kit of two or more separate compartments, including one containing the active ingredients and a second containing a topically/dermatologically-acceptable vehicle, which may be mixed together at some fixed time point prior to application. For example, the active ingredients, in the form of a cream, a powder, a tablet, a capsule or a liquid, may be contained in sealed, single-use packets, which may be opened and mixed with the topically-acceptable vehicle, which may also be stored in pre-measured form in sealed, single-use packets. Alternatively, the active ingredients and the topically-acceptable vehicle may be provided in larger quantities from which the needed amount could be withdrawn using various measuring devices, such as a measuring spoon or cup for solids, or a calibrated vial or dropper for liquids. The extract or compositions of the present invention may be spread onto a substrate and then subsequently packaged. Suitable substrates include dressings, including film dressings, and bandages. In an embodiment, the kit or package may comprise instructions for use/application, e.g., instructions for preventing or reducing a skin condition or disorder such as a skin aging sign or scar or stretchmark.

In an embodiment, the body fluid or extract thereof of the present invention is present in an effective amount to provide a desired result on the skin (e.g., for preventing or reducing a skin aging sign or another skin condition or disorder in a subject). In an embodiment, the body fluid or extract thereof of the present invention is present in a concentration between about 0.01 g/L to about 200 g/L in the skin care composition. In an embodiment, the body fluid or extract thereof of the present invention is present at a concentration between about 0.01% to about 5% w/w of the composition.

In another aspect, the present invention provides the use (e.g., cosmetic or therapeutic use) of the isolated Asteroidea body fluid or extract thereof for preventing or reducing a skin aging sign or another skin condition or disorder in a subject.

In another aspect, the present invention provides a method for preventing or reducing a skin aging sign or another skin condition or disorder in a subject, comprising administering a composition comprising an effective amount of an isolated Asteroidea body fluid or extract thereof on the subject's skin.

In another aspect, the present invention provides the use (e.g., cosmetic or therapeutic use) of the isolated Asteroidea body fluid or extract thereof for preventing or reducing a skin aging sign. Without being so limited, the term "skin condition or disorder" includes skin aging signs, scars such as, but not limited to surgical scars, acne scars and burn scars, and stretch mark wounds such as stretch marks due to pregnancies or other significant weight variations. Without being so limited, as used herein, the terms "skin aging sign" refers to wrinkles, fine lines, scars such as acne scars, stretch mark, loss of skin firmness and elasticity, loss of texture, dehydration, weakening of skin defense mechanism, inflammation, sun damage (particularly UV radiation-induced oxidative stress), redness, telangiectasia, skin sagging, excess sebum, enlarged pores, dark circles, loss of skin firmness, brown spot, age spots, hyper pigmented skin, increased skin thickness, blemishes, loss of skin elasticity and collagen content, dry skin, lentigines, melasmas, dull skin, bags under eyes, lack of sebum, loss of skin comfort and skin devitalization (reduced metabolic activity), or any combination thereof.

As used herein, the terms "reducing" in the expression "reducing skin aging sign" or "reducing skin condition or disorder" is meant to refer to a reduction of a pre-existing aging skin sign, or other skin condition or disorder, respectively. It encompasses complete or partial correction/treatment of the aging sign or other skin condition or disorder, respectively. As used herein, the term "preventing" in the expression "preventing skin aging sign" or "preventing skin condition or disorder" is meant to refer to a delay in the initiation of, or a complete or partial prevention of a skin aging sign, or other skin condition or disorder, respectively.

In an embodiment, the above-mentioned treatment results in one or more of: (a) stimulation of the expression of a gene involved in cellular migration; (b) improved epidermis cell migration; (c) increased collagen fibers thickness; (d) increased number of collagen fibers; (d) reduced keratination of stratum corneum; (e) increased keratinocyte proliferation; (f) increased keratinocyte terminal differentiation; (g) increased epidermis thickness; (h) increased glucosaminoglycans (GAGs) expression; (i) increased density of mitotic cell in epidermis; (j) increased number of epidermis cellular layers; (k) increased expression of at least one of collagen III, collagen IV or collagen VII; (l) reduced crow's feet depth; (m) reduced crow's feet width; (n) increased skin elasticity; (o) reduced mouth wrinkles; (p) increased skin firmness; (q) increased cellular recolonization; and (r) increased skin moisture.

In another aspect, the present invention relates to the use of the isolated Asteroidea body fluid or extract thereof for improving the consistency of collagen fibre structure.

In another aspect, the present invention relates to the use of the isolated Asteroidea body fluid or extract thereof for improving the morphology of stratum corneum and skin texture.

In another aspect, the present invention relates to the use of the isolated Asteroidea body fluid or extract thereof for improving hydration.

In another aspect, the present invention relates to the use of the isolated Asteroidea body fluid or extract thereof for improving skin microrelief.

In another aspect, the present invention relates to the use of the isolated Asteroidea body fluid or extract thereof to promote skin repair functions.

In another aspect, the present invention relates to the use of the isolated Asteroidea body fluid or extract thereof to regulate keratinocyte proliferation and terminal differentiation.

In another aspect, the present invention relates to the use of the isolated Asteroidea body fluid or extract thereof to increase glycosaminoglycans (GAGs) expression.

In another aspect, the present invention relates to the use of the isolated Asteroidea body fluid or extract thereof to promote keratinocyte proliferation.

In another aspect, the present invention relates to the use of the isolated Asteroidea body fluid or extract thereof to increase the expression of collagen. In a further embodiment, the above-mentioned collagen is at least one of collagen III, collagen IV and collagen VII.

In another aspect, the present invention relates to the use (e.g., cosmetic use) of the isolated Asteroidea body fluid or extract thereof for stimulating the expression of one or more gene(s) involved in cellular migration. In a further embodiment, the above-mentioned one or more gene(s) involved in cellular migration is/are coding for Small proline-rich protein(s) (SPRR). In a further embodiment, the above-mentioned SPRR is SPRR2A.

In another aspect, the present invention provides the use of the isolated Asteroidea body fluid or extract thereof for the preparation of a medicament for preventing or reducing a skin condition or disorder such as skin aging sign.

In another aspect, the present invention provides the use of the isolated Asteroidea body fluid or extract thereof for the preparation of a medicament to promote skin repair functions.

In another aspect, the present invention provides the use of the isolated Asteroidea body fluid or extract thereof for the preparation of a medicament for improving the consistency of skin by improvement of collagen fibers structure.

The aging-related skin sign may in more specific embodiments, involve wrinkles, fine lines, age spots, sun damage (particularly UV radiation-induced oxidative stress), blemishes, hyper pigmented skin, increased skin thickness, loss of skin elasticity and collagen content, dry skin, lentigines, and/or melasmas or any combination thereof.

The method of delivery of the extract or compositions of the present invention may vary, but usually involves application to a skin area prone to, or affected by, a skin aging sign, e.g., any skin sign associated with, caused by, or affected by, intrinsic aging and/or extrinsic aging or another skin condition or disorder.

A cream, lotion, gel, ointment, paste or the like may be spread on the affected surface and gently rubbed in. A solution may be applied in the same way, but more typically will be applied with a dropper, swab, or the like, and carefully applied to the affected areas.

The application regimen will depend on a number of factors that may readily be determined, such as the severity of the condition or disorder and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily. Hence as used herein the terms "effective amount" as they relate to a composition of the present invention is an amount that effectively prevents or reduces a skin aging sign or other skin condition or disorder of the subject. It typically constitutes an amount sufficient to cover the skin that is to be treated. The effective amount may vary depending on the form of the composition (e.g., gel, cream, serum, etc.) and the type of skin of the subject.

In an embodiment, the above-mentioned subject is a mammal. In a further embodiment, the above-mentioned mammal is a human.

The present invention is illustrated in further details by the following non-limiting examples.

EXAMPLE 1

Preparation of the Body Fluid Extract

Wild Asteroidea Harvest

Wild Asteroidea (star fish) were trapped and hand picked in bays surrounding Prince-Edward Island. Harvested star fish were of the species *Asteria vulgaris*.

Wild Asteroidea found in Iles-de-la-Madeleine were harvested as a by-catch of scallops dragging activities. The Asteroidea harvested were of the species Crossaster papossus, Leptasterias polaris and *Asterias vulgaris*.

Asteroidea of the *Asteria vulgaris* species were obtained weekly from July to November in Western Prince Edward Island, Canada.

Body Fluid Collection

Body fluid was collected by cutting a piece of the shell and letting the body fluid out by gravity. Body fluids were pooled and then frozen. Alternatively the fluid can be drawn out with a syringe, by centrifugation and by any means providing positive or negative pressure.

Body Fluid Filtration

Frozen body fluid extracts were thawed on ice. All filtration experiments were carried out at 4° C. Body fluid extracts were pre-filtered through a 100 µm syringe-filter then filtered through a 0.22 µm membrane to remove bacteria and ceolomocytes. This filtration produced what is called herein the unfractionated/whole body fluid extract. Ultrafiltration was then carried out. The 0.22 µm filtrate was subject to ultrafiltration on a 50,000 Da cut-off membrane until approximately ⅙ of the initial volume remained above the membrane. An equal volume of saline with a NaCl concentration of approximately 25% that in body fluid (100 mM NaCl) was added to the retentate and filtration was carried out again. Then, saline addition and filtration were repeated. The resulting retentate (>50 kDa fraction) was aliquoted and frozen. The resulting filtrate was then subject to ultrafiltration on a 5,000 Da cut-off membrane until approximately ⅙ of the initial volume remained above the membrane. Equal volume of saline (100 mM NaCl) was added to the retentate and filtration was carried out again. Then, saline addition and filtration were repeated. This second retentate was aliquoted and frozen (5-50 kDa fraction). The final filtrate was then aliquoted and frozen (<5 kDa fraction). All fractions were frozen immediately after their production and stored thereafter at −80° C. until use.

EXAMPLE 2

Effect of the Body Fluid Extract on Cellular Migration a) Principle

Cell migration is an important step of the natural process allowing regeneration and healing of the tissues including scars. With age, this phenomenon tends to slow down in the skin and signs of skin aging take place.

Small proline-rich proteins (SPRR) are encoded by a tandemly arranged four-member gene family (SPRR1-4) contained within a 170-kb region of the epidermal differentiation complex involved in epidermal differentiation. In a previous study published by Demetris et al. (Small proline rich protein (SPRR) function as SH3 domain ligands increase resistance to injury and are associated with epithelial-mesenchymal transition (Net) in cholangiocytes, Journal of Hepatology (2008) 48 (2): 276-288), the hypothesis that SPRR2A expression was wound repair-related has been tested by a Migration Assay. They found that SPPR2A transfectants showed significantly better restitution/migration and increased ability to transverse through the pores of a transwell.

By an analysis of gene expression using dedicated DNA arrays, the Asteroidea body fluid extract has been tested for its effect on the differential expression of genes from reconstructed skin model, and more precisely for the expression of SPRR2A.

b) Protocol

Treatment of Tissues

A fibroblast suspension was prepared in DMEM supplemented with 10% fetal calf serum (FCS) and seeded on the undersurface of the polycarbonate membrane of the reconstructed epidermis (RE) (SkinEthic® Tissues: 112 SkinEthic® reconstructed epidermis (0.50 cm$^2$ and 13 days), batch n° 06 022A 0308 (From SkinEthic Laboratories, France), The co-cultures were incubated for 1 hour at room temperature (cell adhesion) and then placed in 24-well plates containing SkinEthic® growth culture medium supplemented with 2% FCS. After 24 h of incubation, the culture medium was removed and replaced by fresh medium containing or not (control) the unfractionated Asteroidea body fluid extract (2% v/v (i.e. 1150 aqueous dilution of unfractionated extract described in Example 1) (*Asteria vulgaris*), and the co-cultures were incubated for 72 h at 37° C., 5% $CO_2$.

At the end of the culture, the epidermis were removed and washed in PBS buffer. RE submitted to the same treatment were pooled and 1 mL of TRI Reagent™ TRI Reagent™ (Sigma, Saint Quentin, France) was added. Each sample was immediately frozen at −80° C.

The in vitro effect of the extract on cell migration was also assessed by a Migration Assay (scrap test).

Differential Gene Expression Analysis

The analysis of gene expression was performed using standard minichips dedicated to the analysis of gene expression and especially adapted to screening purposes (produced by Bioalternatives). The cDNA arrays used were ATLAS macroarray designed by Bioalternatives (Nice, France) and provided for their exclusive use by Clontech Laboratories, Inc. (Palo Alto, Calif. USA).

These Nylon chips (<3 $cm^2$) were spotted using a spotting device (non-contact spotter, piezo technology, Piezorray, PerkinElmer) and cDNAs specific for markers of interest. The analysis was made using a proprietary technology allowing the miniaturization of the currently used formats and cost-effective analysis. It is based on the use of mRNA as a template for reverse transcription and $^{33}P$ labelling (for optimal sensitivity).

The total RNA of each culture was extracted and purified with TRI Reagent™ according to manufacturer's instructions. Quantity and quality of the purified RNAs were then evaluated using Bioanalyzer Agilent™ 2100.

The multiple cDNA $^{33}P$-labelled targets were prepared by direct reverse-transcription of mRNA, using $[\alpha^{33}P]$-dATP and oligo dT. These labelled cDNA targets were hybridized to the specific cDNA probes covalently fixed to the minichips. After extensive washing, the relative amount of each specific target hybridized to its probe was revealed by PhosphorImaging™.

c) Results

Figure 2:
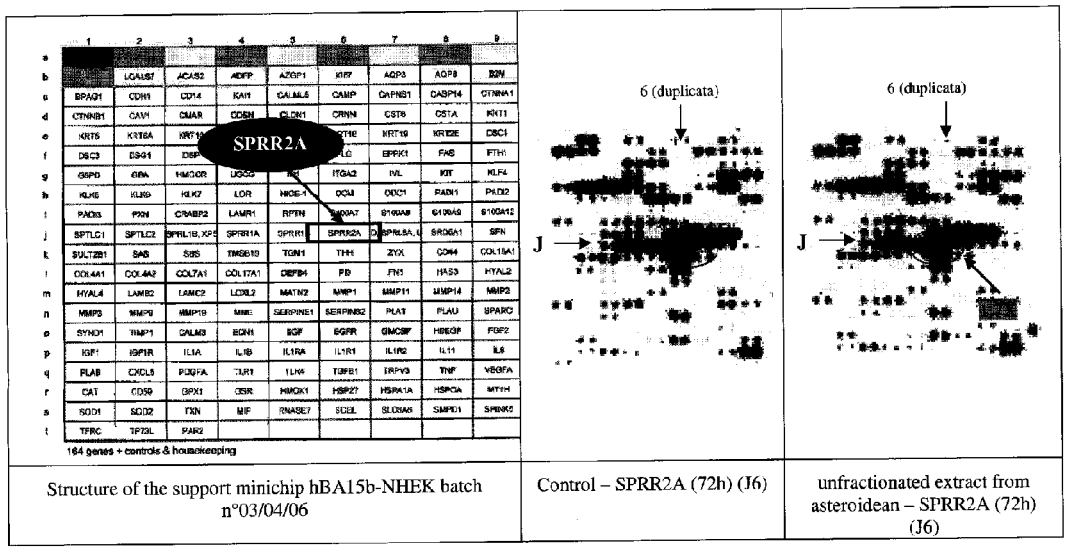
FIG. 2 shows the expression of various genes at day 6 in skin explants treated (middle panel) or not (right panel) with an unfractionated Asteroidea body fluid extract (diluted to 2% v/v in water and culture media). J: day.

As shown in FIG. 2, the body fluid extract from Asteroidea increased the expression of SPRR2A by about 1.7-fold as compared to untreated control. As mentioned above, SPRR2A over-expression is associated with better restitution and cellular migration, which in turn play a role in anti-wrinkle and scars or stretchmarks eraser activity.

EXAMPLE 3

Anti-Aging Effect of a Body Fluid Extract from Asteroidea on Epidermis and Dermis Morphology a) Principle The morphologic observation of the epidermis and dermis on skin explant models provides a good indication of the global effect of a putative anti-aging and anti-wrinkle active ingredient.

In vitro studies on skin explants have been performed in order to assess the regenerative effects of Asteroidea body fluid extracts.

b) Protocol

A carbomer preparation (Carbopol 0.25% w/w; 0.5% w/w; balance to 100% with water) containing 0.5% v/v (1/200 aqueous dilution of unfractionated extract of Example 1) of the unfractionated body fluid or 0.5% w/w of the >50 kDa body fluid fraction were applied topically on in vitro skin explants obtained from a 60-year old woman who underwent abdominal plastic surgery. Retin-OX+™ from ROC was applied as a positive control. These explants were maintained alive in BEM culture medium.

Following paraffin embedding of explants and their Masson's Trichrome staining (day 6), general morphologic observations were realized by optic microscopy (magnification 40).

Epidermal and dermal structures were observed, especially for the number of cellular layers, for the epidermis thickness, for the keratinocytes morphology, for the keratinisation degree of the Stratum corneum and for the papillary dermis collagen fibers density through extracellular matrix.

c) Results

Results of morphologic observations of treated explants were compared to those of non-treated explants and to those of the positive control (Retin-OX+™ from ROC) at day 6.

Figure 3:
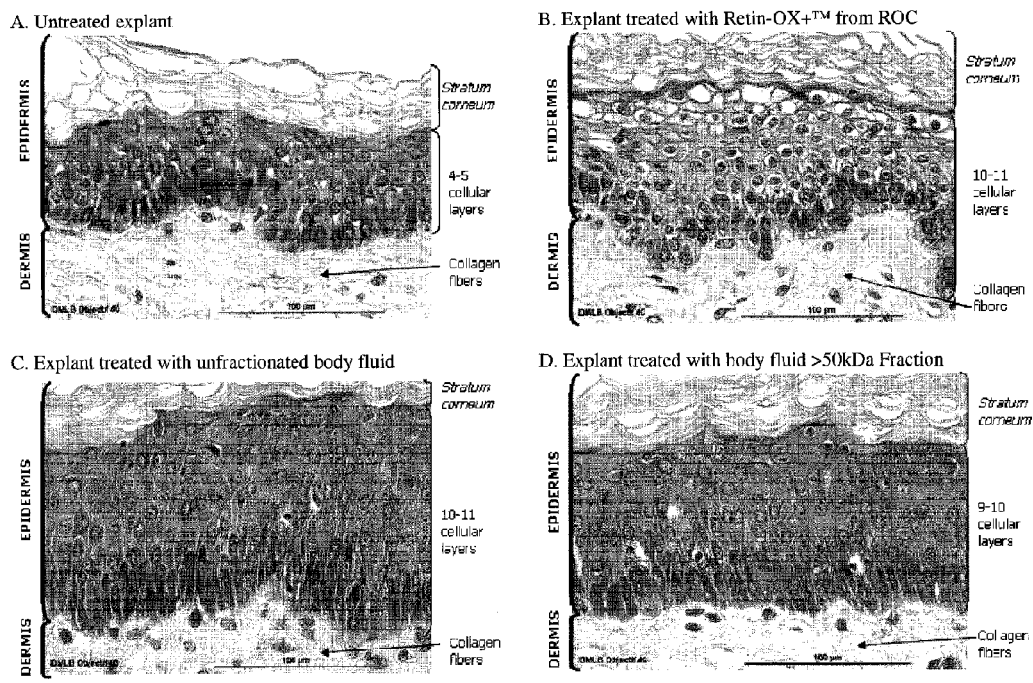
FIG. 3 presents photographs of skin explants either untreated (upper left panel), treated with an unfractionated Asteroidea body fluid extract (lower left panel) treated with fractionated (>50 kDa fraction) body fluid extract from Asteroidea (lower right panel) and treated with Retin-OX+™ (upper right panel)

As shown in FIG. 3, the unfractionated body fluid extract from Asteroidea and the >50 kDa fraction increase the number of cellular layers of the epidermis from 4-5 (control) to 10-11 and 9-10, respectively, without morphologic alterations of keratinocytes (See FIG. 1). Similar results were obtained for Retin-OX+™ (10-11 layers), but with morphologic alterations of keratinocytes (See FIG. 1). For the unfractionated body fluid extract, the >50 kDa fraction and the Retin-OX+™ treated explants, thick collagen fibers located in the papillary dermis provided an extracellular matrix with a higher density than that of untreated explants. Finally, the keratinisation of the Stratum corneum was lower in treated explants (unfractionated body fluid, >50 kDa and Retin-OX+™) than in the untreated one, revealing a regulating effect on keratinocyte proliferation and terminal differentiation as well as an inhibitory effect on the keratinisation process.

These results demonstrate that the body fluid extracts from Asteroidea (both the unfractionated extract and the >50 kDa fraction) have an effect comparable to that of Retin-OX+™ on the epidermis thickness and extracellular matrix collagen (e.g., anti-wrinkle activity), but without cytotoxic effects on keratinocytes.

EXAMPLE 4

Effect of an Asteroidea Body Fluid Extract on Glycosaminoglycans Expression Level a) Principle Glycosaminoglycans (GAGs) possess multiple physiologic roles in the skin. They are known to be excellent dermis water reservoirs and to be good metabolic exchangers, especially for mineral salts, hormones and water. Involved in the collagen maturation and degradation, GAGs are closely linked to these fibers and ensure an optimal organization of extracellular matrix. They also act on cellular growth, by stimulating dermal fibroblasts multiplication, and collagen synthesis.

Since all those physiologic events associated with GAGs are involved in the aging skin and wrinkles formation, the effects of Asteroidea body fluid extracts on GAGs expression was assessed.

b) Protocol

Carbomer preparations as described in Example 3 containing 0.5% v/v of the unfractionated body fluid extract (*Asteria vulgaris*), the >50 kDa, the 5-50 kDa or the <5 kDa fractions were applied topically on in vitro skin explants obtained from a 60-year old woman who underwent abdominal plastic surgery. Using the same procedure, Retin-OX+™ was applied as a positive control. These explants were maintained alive in BEM culture medium.

Paraffin embedding of explants and their Mowry's staining was performed to allow GAGs visualization (day 12). Observations were performed by optic microscopy (magnification 63).

c) Results

Results of GAGs visualization of treated explants were compared to those of non-treated explants and of explants treated with the positive control (Retin-Ox+™) at day 12.

Figure 4:
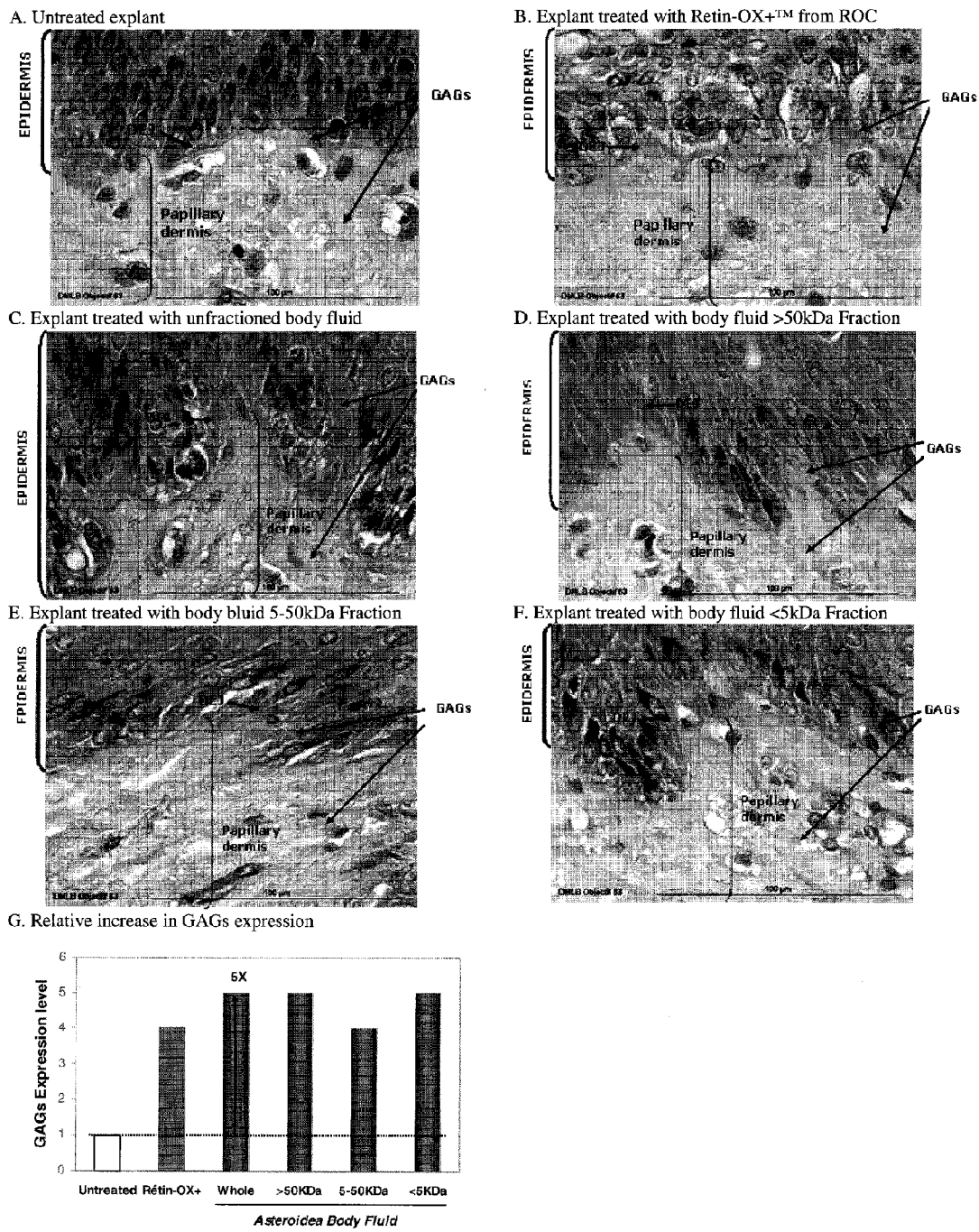
FIG. 4 shows the expression of GAGs in skin explants left untreated (panel A), treated with Retin-OX+™ (panel B), treated with unfractionated Asteroidea body fluid extract (panel C), treated with fractionated (>50 kDa fraction) Asteroidea body fluid extract (panel D), treated with fractionated (5-50 kDa fraction) Asteroidea body fluid extract (panel E) and treated with fractionated (<5 kDa fraction) Asteroidea body fluid extract (panel F). Panel G shows the relative increase in GAGs expression in treated explants as compared to untreated explants. Dej: dermal-epidermal junction.

As shown in FIG. 4, panel G the Asteroidea body fluid extract increased the expression of the GAGs by about 5-fold, for the unfractionated extract and for the >50 kDa and <5 kDa fractions, and by about 4-fold for the 5-50 kDa fraction and Retin-OX+™. This is characterised by a regular and thick pink to purple band (Only seen on color photography) on the edge of the dermo-epidermal junction and in the papillary dermis.

EXAMPLE 5

Effect of an Asteroidea Body Fluid Extract on Cellular Proliferation a) Principle Cellular renewal can be measured by an ex vivo model technique. Immunoblotting of Ki67, a mitotic cell marker, is used to get quantitative data on cell proliferation.

The objective of this study was to assess the proliferating effect of Asteroidea body fluid extracts on skin cells.

b) Protocol

A carbomer preparation as described in Example 3 containing 0.5% v/v of the unfractionated body fluid (i.e. dilution 1/200 of unfractionated extract of Example 1) (*Asteria vulgaris*), the >50 kDa, the 5-50 kDa or the <5 kDa fraction was applied topically on in vitro skin explants obtained from a 60-year old woman who underwent abdominal plastic surgery. Using the same procedure, Retin-OX+™ was applied as a positive control. These explants were maintained alive in BEM culture medium.

Ki67 immunoblotting on frozen explants (Day 6) slices was performed with anti-Ki67 monoclonal antibody and with biotin/streptavidin as a signal amplifying system. Nucleus staining was made with Masson's hemalun. This method allows mitotic cell visualization. Observations were performed by optic microscopy (magnification 20 or 40) and stained cells were then counted. The results were expressed as the number of stained cells by centimeter (cm) of epidermis (mean).

c) Results

Results of Ki67 immunoblotting of treated explants were compared to those of non-treated explants and explants treated with the positive control (Retin-Ox+™) at day 6.

Figure 5:
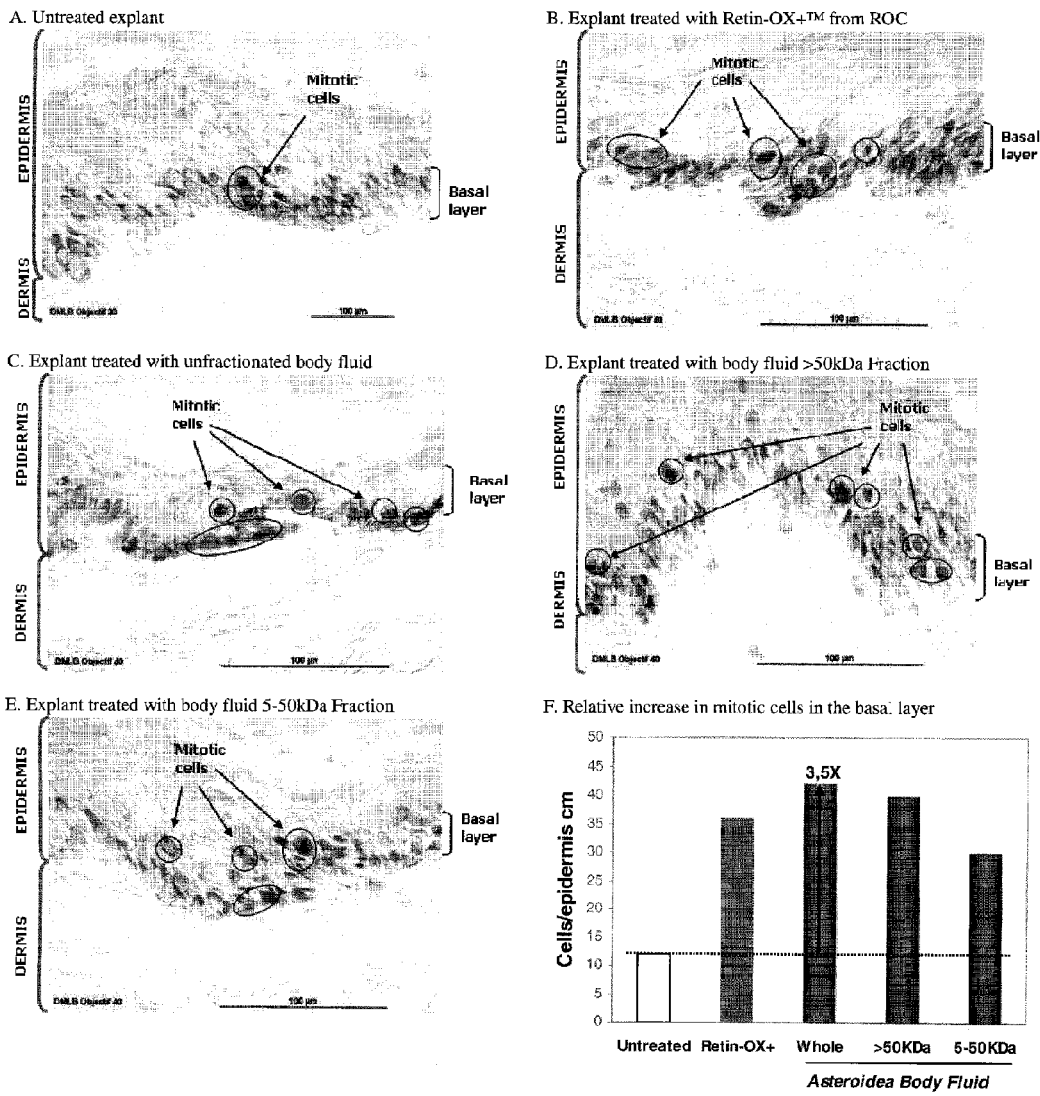
FIG. 5 shows the number of mitotic cells in basal layer in skin explants untreated (panel A), treated with Retin-OX+™ (panel B), treated with unfractionated Asteroidea body fluid extract (panel C), treated with fractionated (>50 kDa fraction) Asteroidea body fluid extract (panel D), and treated with fractionated (5-50 kDa fraction) Asteroidea body fluid extract (panel E). Panel F shows the relative increase in the number of cells in the epidermis in treated explants as compared to untreated explants.

The Asteroidea body fluid extracts (the unfractionated extract as well as the >50 kDa and 5-50 kDa fractions) increased the number of mitotic cells in the explants (FIG. 5). The number of mitotic cells per centimeter of epidermis was about 3.5-, 3.3- and 2.5-fold (3-fold for Retin-OX+™) higher in the explants treated with the unfractionated, the >50 kDa and the 5-50 kDa fractioned body fluid extracts, respectively, when compared to the untreated explants.

These results show that Asteroidea body fluid extracts have an effect on keratinocytes proliferation, which in turn allows a better regeneration of the epidermis, giving thickness and strength to this part of the skin (e.g., anti-wrinkles properties).

EXAMPLE 6

Effect of an Asteroidea Body Fluid Extract on Collagen III Expression a) Principle This study consisted in the assessment of the effect of Asteroidea body fluid extracts on collagen III production. With age, collagen III production decreases, causing the apparition of skin-aging signs.

Collagen III produced by fibroblast cells is a fibrilar collagen type present in the extracellular matrix of the dermis, and its main role is to form a network structure that gives firmness to the skin.

b) Protocol

Carbomer preparations as described in Example 3 containing 0.5% v/v of the unfractionated body fluid (i.e. dilution 1/200 of unfractionated extract of Example 1) (*Asteria vulgaris*), the >50 kDa, the 5-50 kDa or the <5 kDa fraction were applied topically on in vitro skin explants obtained from a 60-year old woman who underwent abdominal plastic surgery. Using the same procedure, Retin-OX+™ was applied as a positive control. These explants were maintained alive in BEM culture medium.

Collagen III Immunoblotting on frozen explants (Day 6) slices was performed with an anti-collagen III polyclonal antibody and a DAB revelation kit. Cells were stained with Masson's hemalun. This method allowed collagen III visualization in papillary dermis.

Observations were performed by optic microscopy (magnification 40).

c) Results

Results of Collagen III visualization of treated explants were compared to those of non-treated explants (days 6) and explants treated with the positive control (Retin-Ox+™) at day 6.

Figure 6:
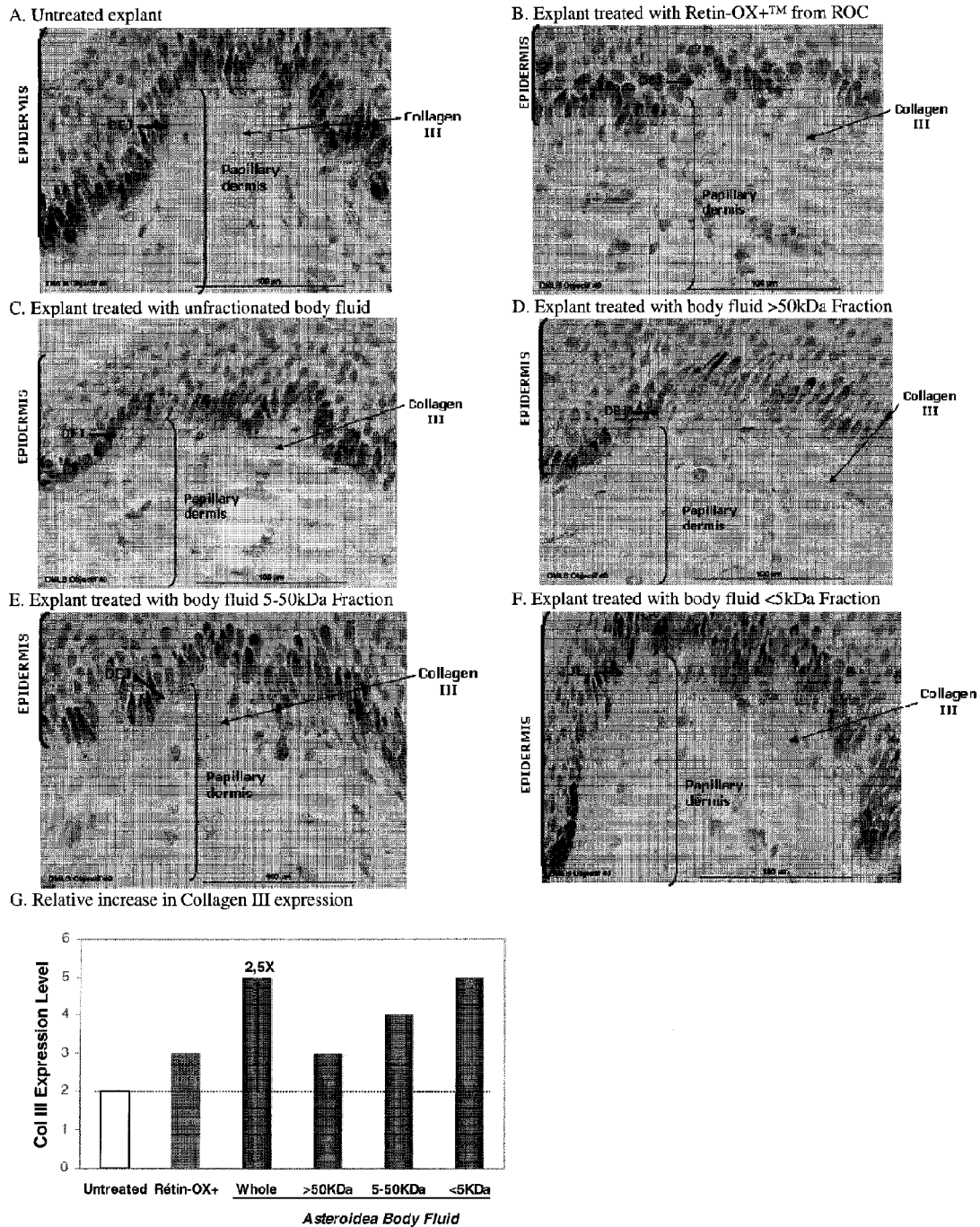
FIG. 6 shows the expression of Collagen III in skin explants left untreated (panel A), treated with Retin-OX+™ (panel B), treated with unfractionated Asteroidea body fluid extract (panel C), treated with fractionated (>50 kDa fraction) Asteroidea body fluid extract (panel D), treated with fractionated (5-50 kDa fraction) Asteroidea body fluid extract (panel E) and treated with fractionated (<5 kDa fraction) Asteroidea body fluid extract (panel F). Panel G shows the relative increase in Collagen III expression in treated explants as compared to untreated explants.

As shown in FIG. 6, the unfractionated and the fractioned Asteroidea body fluid extracts increased the expression of collagen III. Collagen III is overexpressed by about 2.5-, 1.5-, 2.0- and 2.5-fold in explants treated with the unfractionated body fluid extract, the >50 kDa, the 5-50 kDa and the <5 kDa fractions, respectively. The increase was about 1.5-fold for the explants treated with Retin-OX+™.

These results demonstrated that the Asteroidea body fluid extracts have an effect on Collagen III expression, which in turn plays a role in anti-wrinkle and acne scars or stretchmarks eraser activity.

EXAMPLE 7

Effect of an Asteroidea Body Fluid Extract on Collagen IV Expression a) Principle This study consisted in the assessment of the effect of Asteroidea body fluid extracts on collagen IV production. With age, collagen IV production decreases, causing the apparition of skin-aging signs.

Collagen IV production by both keratinocytes and fibroblasts takes place in the basal membrane of the epidermis. Collagen IV plays a role in mechanical stability of the skin.

b) Protocol

Carbomer preparations as described in Example 3 containing 0.5% v/v of the unfractionated body fluid extract (i.e. dilution 1/200 of unfractionated extract of Example 1) (*Asteria vulgaris*), the >50 kDa, the 5-50 kDa or the <5 kDa fraction were applied topically on in vitro skin explants from a 60-year old woman who underwent abdominal plastic surgery. Using the same procedure, Retin-OX+™ was applied as a positive control. These explants were maintained alive in BEM culture medium.

Collagen IV Immunoblotting on frozen explants (Day 6) slices was performed with an anti-collagen IV polyclonal antibody and an FITC revelation kit. Cells were stained with Propidium iodure. This method allowed collagen IV visualization in the derma-epidermal junction, the papillary dermis and around cutaneous annexes.

Observations were performed by optic microscopy (magnification 40).

c) Results

Results of Collagen IV visualization of treated explants were compared to those of non-treated explants (days 6) and explants treated with Retin-Ox+™

Figure 7:
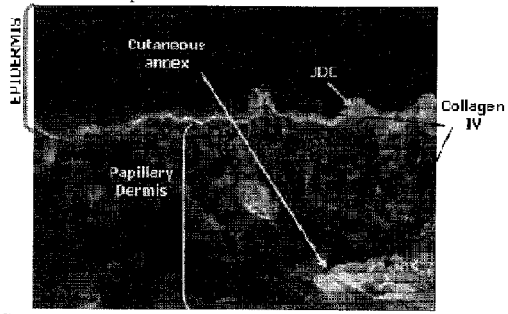
FIG. 7 shows the expression of Collagen IV in skin explants left untreated (panel A), treated with Retin-OX+™ (panel B), treated with unfractionated Asteroidea body fluid extract (panel C), treated with fractionated (>50 kDa fraction) Asteroidea body fluid extract (panel D), treated with fractionated (5-50 kDa fraction) Asteroidea body fluid extract (panel E) and treated with fractionated (<5 kDa fraction) Asteroidea body fluid extract (panel F). Panel G shows the relative increase in Collagen IV expression in treated explants as compared to untreated explants.
Figure 7:
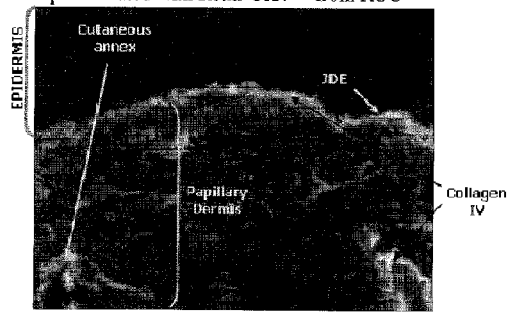
Figure 7:
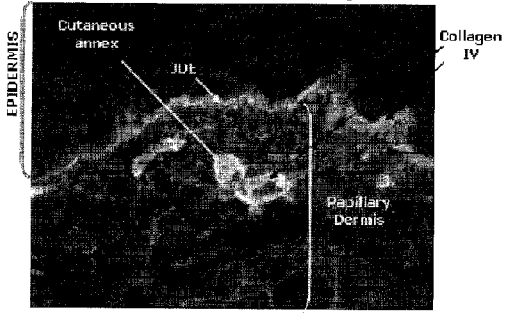
Figure 7:
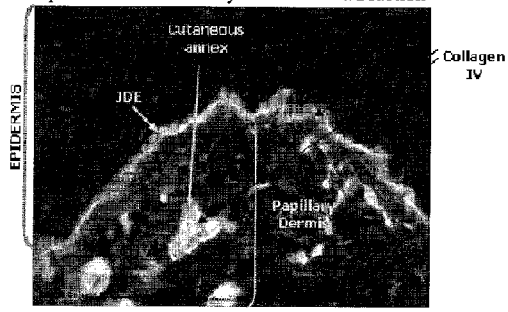
Figure 7:
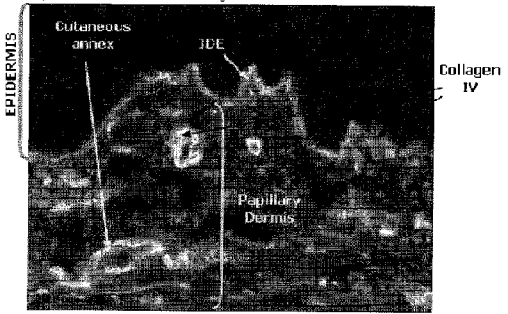
Figure 7:
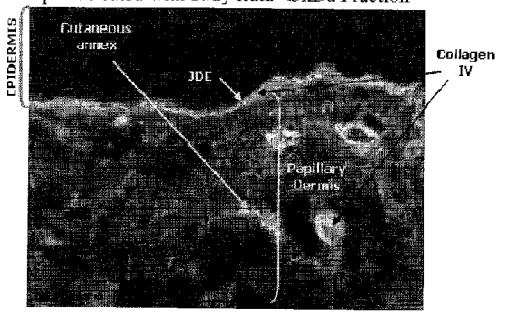
Figure 7:
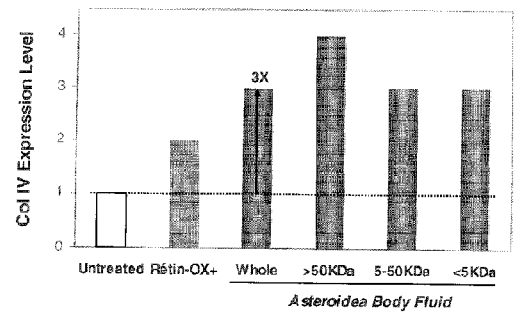

As shown in FIG. 7, the unfractionated and the fractioned Asteroidea body fluid extracts increased the expression of collagen IV. Collagen IV was overexpressed by about 3.0-, 4.0-, 3.0- and 3-fold in explants treated with the unfractionated body fluid extract, the >50 kDa, the 5-50 kDa and the <5 kDa fractions, respectively. The increase was about 2 fold for the explants treated with Retin-OX+™

These results demonstrate that the Asteroidea body fluid extracts have an effect on Collagen IV expression, which in turn plays a role in anti-wrinkle and acne scars or stretch-marks eraser activity.

EXAMPLE 8

Effect of an Asteroidea Body Fluid Extract on Collagen VII Expression a) Principle This study consisted in the assessment of the effect of Asteroidea body fluid extracts on collagen VII production. With age, collagen VII production decreases, causing the apparition of skin-aging signs.

Collagen VII is produced mainly by keratinocytes and is an anchoring fibril collagen type presents in dermo-epidermal junction. Collagen VII plays a role in stabilizing the association of the basement membrane to the underlying dermis, and consequently contributes to the integrity of the cutaneous basement membrane.

b) Protocol

A carbomer preparation as described in Example 3 containing 0.5% v/v (i.e. dilution 11200 of unfractionated extract of Example 1) of the >50 kDa or the <5 kDa fraction of the Asteridea body fluid extract (*Asteria vulgaris*), was applied topically on in vitro skin explants obtained from a 60-year old woman who underwent abdominal plastic surgery. Using the same procedure, Retin-OX+™ was applied as a positive control. These explants were maintained alive in BEM culture medium.

Collagen VII Immunoblotting on frozen explants (Day 6) slices was performed with an anti-collagen VII monoclonal antibody and biotin/streptavidin as a signal amplifying system and FITC revelation kit. Cells were stained with Propidium iodure. This method allows collagen VII visualization in the dermo-epidermal junction.

Observations were performed by optic microscopy (magnification 40).

c) Results

Results of Collagen VII visualization of treated explants were compared to those of non-treated explants (days 6) and of explants treated with Retin-Ox+™ at day 6.

Figure 8:
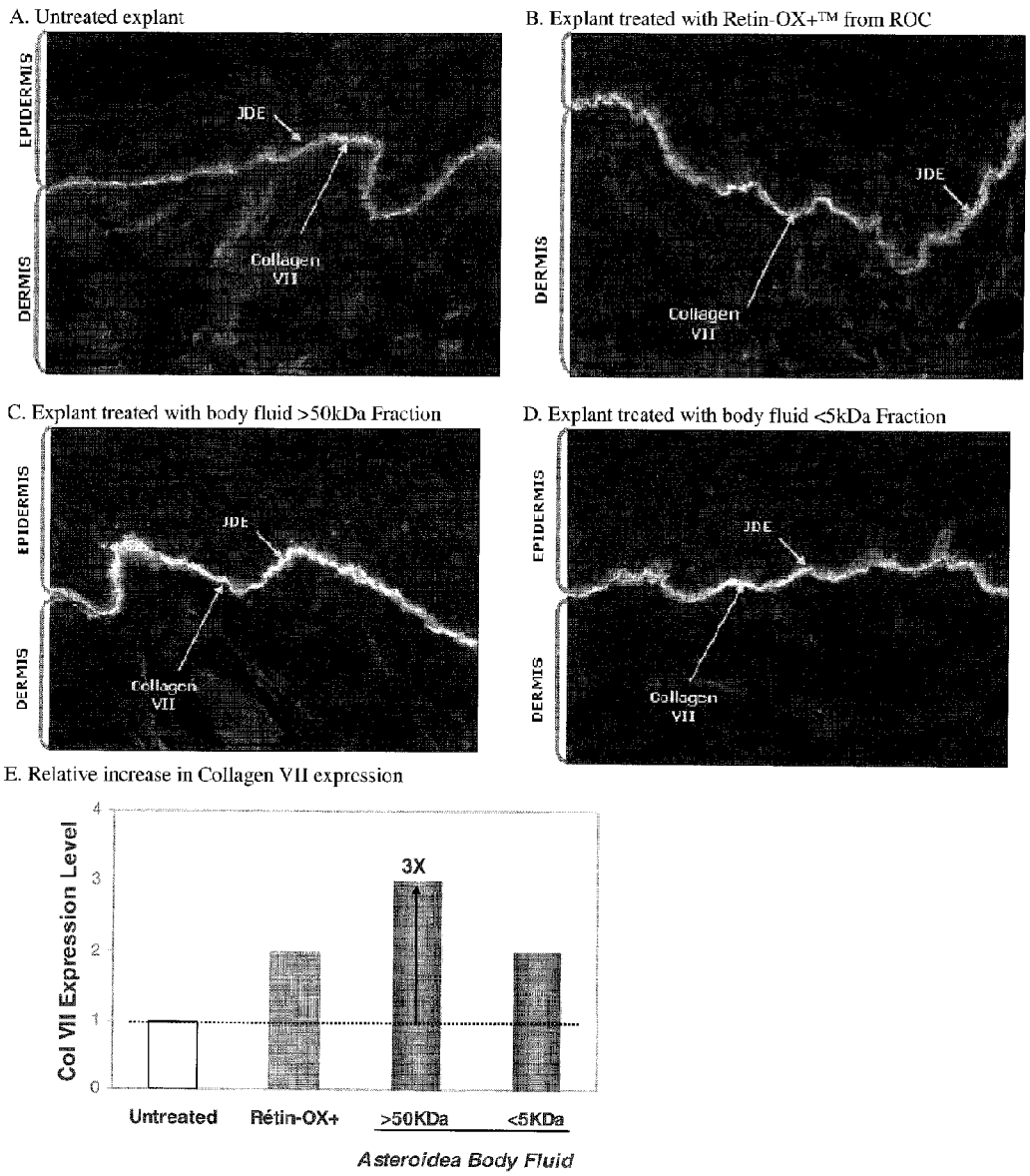
FIG. 8 shows the expression of Collagen VII in skin explants left untreated (panel A), treated with Retin-OX+™ (panel B), treated with fractionated (>50 kDa fraction) Asteroidea body fluid extract (panel C), and treated with fractionated (<5 kDa fraction) Asteroidea body fluid extract (panel D). Panel E shows the relative increase in Collagen VII expression in treated explants as compared to untreated explants.

As shown in FIG. 8, the >50 kDa and the <5 kDa fractions of the Asteroidea body fluid extract increased the expression of collagen VII. Collagen VII was overexpressed by about 3.0- and 2.0-fold, respectively, in the explants treated with the >50 kDa and the <5 kDa fractions of the body fluid extract. The increase was about 2.0-fold for the explants treated with Retin-OX+™

These results demonstrate that the Asteroidea body fluid extracts have an effect on Collagen VII expression, which in turn plays a role in anti-wrinkle and acne scars or stretch-marks eraser activity.

EXAMPLE 9

Efficacy of a Body Fluid Extract from Asteroidea on Skin Improvement of Human Voluntaries Thirty middle-aged and aged Caucasian women, 45- to 70-year old (volunteers), topically applied twice daily on half of their face a cream containing 0.5% v/v (i.e. 1/200 aqueous dilution of unfractionated extract of Example 1) Asteroidea body fluid extract (*Asteria vulgaris*) (<0.22 μm fraction) (see Table I below for composition of cream) for a period of 28 days. To obtain a placebo-controlled study, the other half of the face received the same cream without any active ingredient. All voluntaries had wrinkles and fine lines around the eyes (crow's feet). The anti-wrinkle activity, the firmness activity, the elasticity activity, the moisturizing activity and the effect on desquamation of the Asteroidea body fluid extract was assessed.

TABLE I

Active cream composition

| Ingredient | Supplier | % w/w |
|---|---|---|
| Demineralized water (Aqua) | Les eaux saint-Léger | q.s. ad 100% |
| Carbopol ™ Ultrez-10 (Carbomer) | Noveon | 0.15 |
| Propylenglycol | Brenntag | 3.00 |
| Phenonip ™ (Phenoxyethanol, Methylparaben, Ethylparaben, Butylparaben, Propylenparaben, Isobutylparaben) | Nipa | 0.80 |
| Emersol ™ 132 (Stearic acid) | Cognis | 1.00 |
| Cutina ™ MD (Glyceryl Stearate) | Cognis | 4.00 |
| Lanette ™ 16 (Cetyl Alcohol) | Cognis | 1.00 |
| Arlacel ™ 60 (Sorbitan Stearate) | Uniquema | 0.50 |
| Cetiol ™ CC (Dicaprylyl Carbonate) | Cognis | 2.00 |
| Myritol ™ 312 (Caprylic/Capric Triglycerides) | Cognis | 5.00 |
| Dermowax ™ MM (Myristyl Myristate) | Multichem | 3.00 |
| Tween ™ 60 (Polysorbate 60) | Uniquema | 2.00 |
| Karite butter (*Butyrospermum Parkii*) | Multichem | 1.00 |
| SF-96-350 (Dimethicone) | Demsey Corp. | 0.04 |
| Triethanolamine 99 (Triethanolamine) | Dow Chemical | 0.15 |
| Fragrance No 6122 Floral citrus (Parfum) | Fleurarôme | 0.04 |
| Coelomic fluid from *Asteria vulgaris* | Les Biotechnologies Océanova Inc. | 0.50 |

At the beginning of the test (D0), the volunteers went to the laboratory on appointment days. Each volunteer first signed the participation consent form. The dermatologist performed the dermatologic examination. The technician took imprints of crow's feet areas and noted hydration and firmness/elasticity measures. At the end of the test (D28), the dermatologist performed the dermatologic examination. The technician took once again the imprints of crow's feet areas and noted hydration and firmness/elasticity measures.

Anti-Wrinkle Assessment

Biometrological measures using the fringe projection technique, were used to evaluate the anti-wrinkle effect of the active cream. The depth, width and volume of wrinkles were thus measured using the fringe projection technique.

The DermaTOP™ system developed by Eotech, is based on interference fringe projection profilometry associated with the Toposurf™ surface processing software. All data are calculated with the software Optocat™, from DermaTOP™ data acquisition and treatment system. These 3D reconstructions are then analyzed with the software Toposurf™, which allows calculating the mean depth, mean width and mean volume of wrinkles.

Mean values obtained from depth, width and volume values of wrinkles were calculated for each subject, before and after application of the tested product. The overall effect of the tested product was calculated by determining the percentage of variability in comparison with initial measure, from mean values and for each parameter. Results were analyzed and interpreted according to data obtained in adopted experimental conditions. The test performed was the Student's t test on paired data. The application conditions were the nature of simple random sampling and the normality of population distributions.

Figure 9:
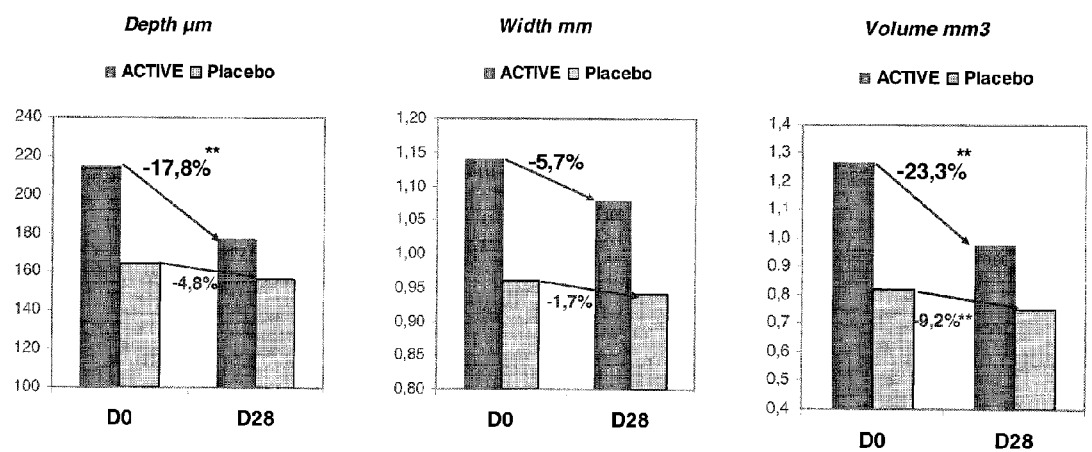
FIG. 9 compares the anti-wrinkle effect of a composition of the present invention with that of a placebo on the skin of volunteers after 28 days of treatment.
Figure 10:
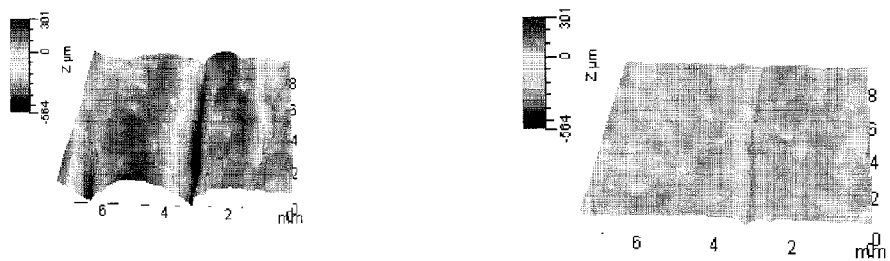
FIG. 10 compares the anti-wrinkle effect of a composition of the present invention with that of a placebo on the skin of volunteers after 28 days of treatment.
Figure 10:
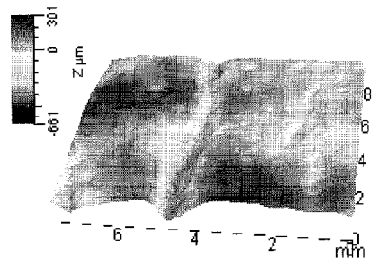
Figure 10:
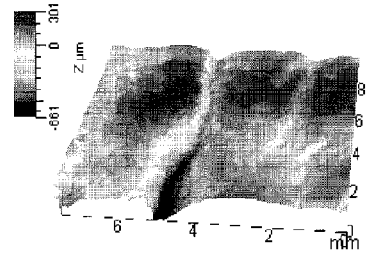

Results:

As may be observed in FIGS. 9-10, after 28 days of application of active cream (0.5% w/w coelomic fluid<0.22 µm), a reduction of 17.8% of the depth, 5.7% of the width and 23.3% of the volume of wrinkles was observed. For the placebo, values were lower and not significant for the depth and width. Although the reduction of the volume was significant, it was more than two times less important than with the active cream.

Moisture Assessment

The hydrating/moisturizing effect of Asteroidea coelomic liquid was also evaluated. Skin hydration was measured by corneometry. The measuring principle is based on capacitance measurement of a dielectric medium, or the measuring principle of the Corneometer™. Stratum corneum is characterized by a dielectric mean value. The dielectric properties of the stratum corneum are determined by its level of hydration. The equipment measures the corresponding capacitance.

The test performed was the Student's t test on paired data.

Figure 11:
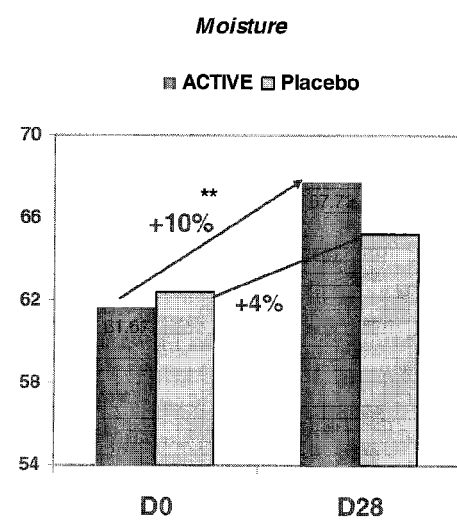
FIG. 11 compares the skin moisturizing effect of a composition of the present invention with that of a placebo on the skin of volunteers after 28 days of treatment.

Results:

As may be observed in FIG. 11, after 28 days of application of active cream (0.5% w/w coelomic fluid<0.22 µm), a significant increase of 10% of cutaneous hydration was observed. An increase was also noticeable with the placebo but it was not statistically significant and it was much weaker than with the active.

Firmness and Elasticity Assessment

The effect of the active cream on mechanical properties, firmness and elasticity of the skin was also evaluated.

Firmness and elasticity properties of the skin were measured via cutometry. The evaluation of mechanical properties allows studying the functional level of responsible structural tissues: the elastic structures (elastic fibers, curve of conjunctive fibers, folding of stratum corneum) and the structures having a viscous behaviour (interstitial fluids and internal adhesions).

The study was performed using the cutometer MPA 580® (*Courage & Khazaka Electronic*). The measuring principle is based on the suction (aspiration) method. Negative pressure is created in the device—two prisms facing each other—and the skin is drawn into the 2 mm aperture of the probe. Inside the probe, the penetration depth is determined by a non-contact optical measuring system. The skin is lifted, stretched and then released. The resistance of the skin to be sucked up by the negative pressure (firmness) and its ability to return into its original position (elasticity) allows to see its firmness, elasticity and its viscous behaviour, which is a good overall indication of cutaneous tonicity.

When the skin is released and returns to its normal position, immediate total recovery measures pure cutaneous elasticity (measured by R6), while delayed recovery measures its viscoelasticity component (measured by R7).

R0: This parameter represents skin firmness, which is the passive response of the skin to applied force. The more the skin is firm, the greater this parameter will be.

R6: This parameter represents skin elasticity. The more the value of this parameter is low, the more the skin is elastic.

R7: This parameter also represents skin elasticity. The more the value of this parameter tends towards 1, the more the skin is elastic. In the case the cutaneous elasticity is improved, the level of immediate recovery tends towards starting point, which means that R7 will increase.

Figure 12:
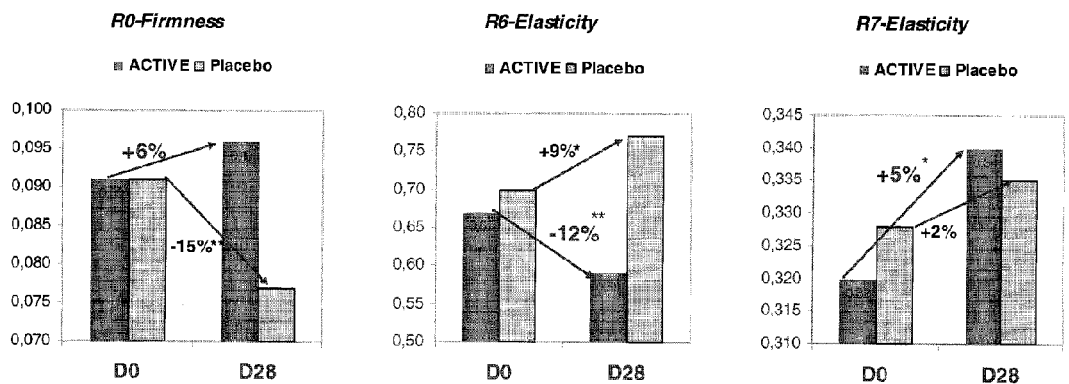
FIG. 12 compares the effect on skin firmness (R0 parameter) and elasticity (R6 and R7 parameters) of a composition of the present invention with that of a placebo on the skin of volunteers after 28 days of treatment.

Results:

As may be observed on FIG. 12, after 28 days of application of active cream (0.5% w/w coelomic fluid<0.22 µm), parameters R0 and R7 increased by 6% and 5% respectively. With the placebo, a decrease in parameter R0 and a very slight, non-significant increase of parameter R7 was observed. As for parameter R6, a 12% decrease was registered, in comparison with a 9% increase for the placebo. The coelomic liquid of the Asteroidea has a significant and non-neglectable improving effect over 28 days on the elasticity and firmness of the skin when compared to that of the placebo.

Evaluating the State of Physiological Desquamation

The effect of Asteroidea coelomic liquid/body fluid on the state of physiological desquamation of the skin was evaluated.

The evaluation of cutaneous hydration with the system named DIAGNOSKIN® is performed by objectivating the physiological desquamation. A flexible tape (D-Squames®), affixed on the skin, retains the superficial layer of corneocytes when it is removed. The semiologic evaluation of this desquamation with an optical microscope (objective×25 with cold light) leads to quoted values from 1 to 12, increasing according to the level of hydration.

The hydration of the stratum corneum and the quality of physiological desquamation of the corneocytes are actually two parameters that are intimately related: an abnormal desquamation leads to a disruption of the water barrier function and consequently to a dehydration tendency of the stratum corneum, and a cutaneous dryness is able to disturb the desquamation process. This intimate linkage of the water content of the stratum corneum and the desquamation process was confirmed by a comparative evaluation of corneometric and squamometric data obtained with the semiologic exploitation named DIAGNOSKIN® (an exclusivity of BIO-EC, France) (GASSER P., PENO-MAZZARINO L., LATI E., DJIAN B. Original semiologic standardized evaluation of stratum corneum hydration by Diagnoskin® stripping sample. International Journal of Cosmetic Science, 2004, 26, 117-127). This validates DIAGNOSKIN® as a system to evaluate the level of cutaneous hydration.

Results

Figure 13:
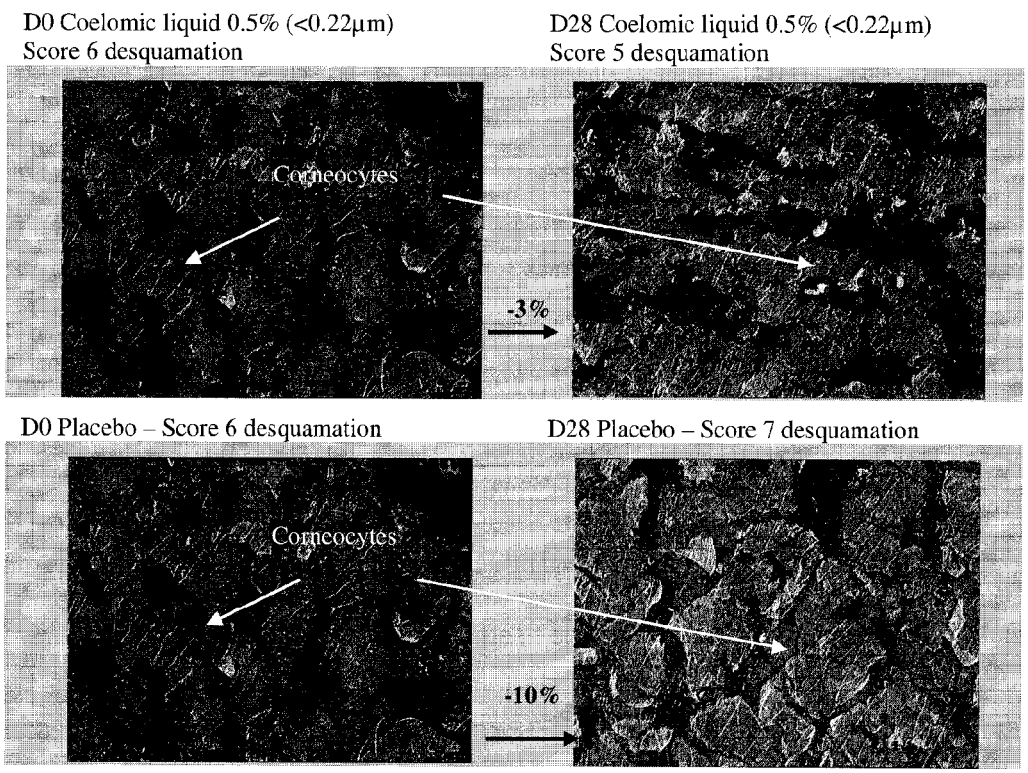
FIG. 13 compares the effect on physiological desquamation of a composition of the present invention with that of a placebo on the skin of volunteers after 28 days of treatment.

As may be observed in FIG. 13, the quality of desquamation was reduced by 3% after 28 days of application of the active cream (0.5% w/w coelomic liquid<0.22 µm). Since this reduction is not statistically significant, it is possible to assert that the coelomic liquid does not affect the state of desquamation of the skin, unlike the placebo which caused a 10% reduction of the quality of desquamation.

EXAMPLE 10

Effect on Cellular Migration or Recolonization of Asteroidea Body Fluid Extract a) Principle Cell migration is an important step of the natural process allowing regeneration and healing of the tissues including acne and stretchmark wounds. With age, this phenomenon tends to slow down in the skin and signs of skin aging take place.

b) Protocol

Confluent monolayers of normal human keratinocytes were obtained by culturing cells taken from a 30 year old woman. Once the confluence was obtained, a "scrap" (or "injury") was realized in each culturing well by scratching the cellular mat. The remaining cells were then incubated in absence (control) or in presence of increasing concentrations of Asteroidea coelomic liquid (fraction 5-50 kDa and <5 kDa) or reference product. The reference product used in this study was the Transforming Growth Factor β (TGF-β) at 10 ng/ml. Cells were incubated at 37° C., on humid atmosphere and 5% of $CO_2$, in absence or in presence of the Asteroidea coelomic liquid (fraction 5-50 kDa and <5 kDa) at increasing concentrations. After 48 hours of incubation, the effects of the tested coelomic liquid were evaluated.

Evaluation of the Effects

"Injured" surfaces at D0 and at the end of incubation period (non-recolonized injury surface) were measured with software for image analysis (Image J™).

Statistics

Results are given as a percentage of the recolonized surface in comparison with the "Control" condition, and according to the photographic fields that were observed. The statistical significance of the differences observed between the conditions "Witness" and "coelomic liquid" was evaluated product by product, by the analysis of the variance of one factor (One-Way ANOVA or One Way Anova on Ranks+), followed, if necessary, by a Holm-Sidak or a Dunn's test (*:$p<0.05$).

c) Results

Figure 14:
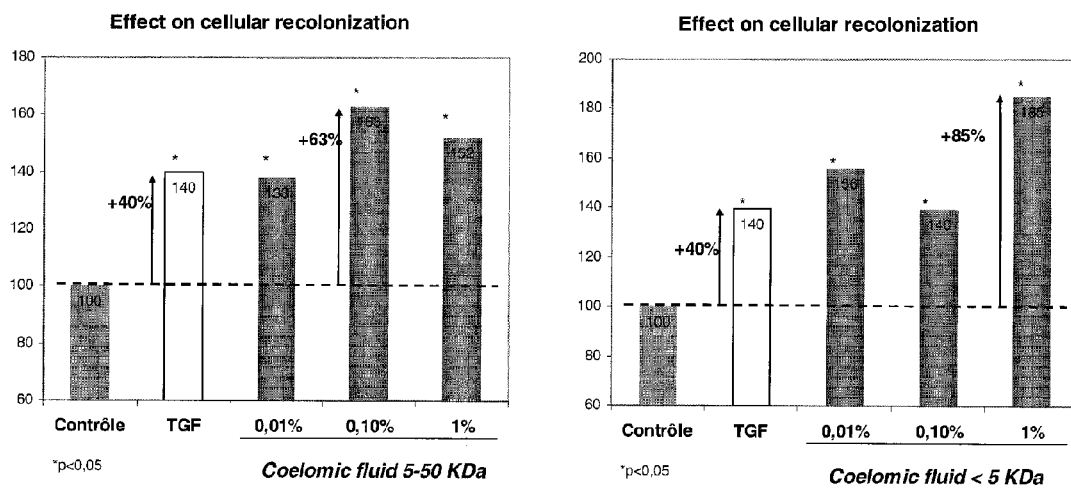
FIG. 14 shows the effect of coelomic fluid fractions of 5-50kDa and of <5 kDa on cellular recolonization of human normal keratinocytes of a 30 year old women.

For the two fractions that were tested in the scrap test, a positive effect was observed on cellular recolonization in vitro (FIG. 14). For the cells that were treated with coelomic liquid, 5-50 kDa fraction, compared with non-treated cells, there was an increase of cellular recolonization by 38%, 63% and 52% for doses of 0.01% v/v, 0.1% v/v and 1% v/v respectively. For the cells that were treated with coelomic liquid, fraction <5 kDa, compared with the non-treated cells, there was an increase in cellular recolonization by 56%, 40% and 85% for doses of 0.01% v/v, 0.1% v/v and 1% v/v respectively. All these results are equal or superior to the positive control (TGF 10 ng/ml), which increased cellular recolonization by 40%, and are all statistically significant.

By its effect on cellular migration, the body fluid from Asteroidea, according to this invention, has a potential wound healing, cicatrizing, anti-wrinkle and "acne scars or stretch marks eraser" activity.

EXAMPLE 11

Human TGF-β1 Detection in Asteroidea Body Fluid Extract a) Principle

Growth factors are natural substances important for regulating a variety of cellular processes. They typically act as signalling molecules between cells. They often promote cell differentiation and maturation, which varies between growth factors.

More specifically, Transforming growth factor beta (TGF-β) controls proliferation, cellular differentiation, and other functions in most cells. Some cells secrete TGF-β, and also have receptors for TGF-β. This is known as autocrine signalling. TGF-β is a secreted protein that exists in three isoforms including TGF-β1.

Morphollaxy, the mechanism by which seastars rapidly regenerate a loosen part, is dependent on three classes of regulating substances including Growth Factor-Like molecules (e.g., TGF-β, NGF, RGF-2 (basic fibroblast growth factor)). Those molecules are present at the tissue and organic fluid level in the Asteroidea.

Detection of TGF-β was determined to establish a relation between effect on human skin of Asteoidea coelomic fluid and its molecular composition.

b) Protocol

The method selected was an ELISA, enzyme-linked immunosorbent assay, kits manufactured by R&D Systems Inc Company.

The Quantikine® human TGF-β1 Immunoassay kit (#DEB100B) that was used employs the quantitative sandwich enzyme immunoassay technique. Monoclonal antibodies specific against TGF-β1 were pre-coated into microplates. Standards and Asteoidea coelomic fluid were delivered into wells. All molecules of human TGF-β1 present within these samples were bound to immobilize antibodies. After washing away any unbound molecules, enzyme-linked polyclonal antibodies specific against TGF-β1 were added to wells. Following washing and color development steps, optical density of each well was determined by spectrophotometry ($\lambda=450$ nm and $\lambda=540$ nm). Background, represented by optical density values obtained at $\lambda=540$ nm, was subtracted from the optical density values obtained at $\lambda=450$ nm.

The possible occurrence of any interference that may affect the performance of the test by molecules present in the product of the present invention has also been evaluated. A known concentration of TGF-β1 (125 pg/ml) was spiked in some of the samples. A comparison in optical density values between the standard condition versus Asteroidea coelomic fluid samples with or without the presence of the standard. An absence of interference generates data of similar level in "standard" and "spiked-sample with standard" conditions.

Step A-Original Asteroidea coelomic fluid: Five representative samples (i.e. sampled monthly from May to October) of the Asteoidea coelomic fluid were assayed. The experimental condition consisted of using the assay diluent RD1-73 for serum/plasma type samples. Three serial dilutions of the Asteoidea coelomic fluid were performed since the recommended dilution rate is of 1/20 in the kits. The serial dilutions 1/2 (50% v/v) and 1/10 (10% v/v) and 1/20 (5% v/v) were used.

Step B-Lyophilized Asteroidea coelomic fluid: In order to obtain more concentrated samples and to confirm the results of step A, the Asteroidea coelomic fluid has been lyophilized prior to analysis (step-B).

The same five representative samples of the Asteoidea coelomic fluid were assayed. These five samples were in lyophilized powder form and were dissolved with 3.5 ml of assay buffer RD5-53. The assay diluent RD1-73 for serum/plasma type samples was used. Three serial dilutions of the Asteoidea coelomic fluid were performed since the recommended dilution rate is 1/20 in the kits. The serial dilutions 1/2 (50% v/v), 1/4 (25% v/v) and 1/40 (2.5% v/v) were used.

Standard curves were created by plotting TGF-β1 concentrations in axe "X" versus Optical Density values in axe "Y" and the best-fit line is determined by regression analysis. All samples were tested in duplicate and were dissolved in appropriate solutions. Data average was expressed as mean±S.D.

c) Results

Step A. Detectable level of TGF-β1 within the Asteoidea coelomic fluid was observed but the data are not significant (between 2 and 7 pg/ml). In order to validate the presence of TGF-β1 within the Asteoidea coelomic fluid the experiment was repeated with lyophilised samples (Step B).

Step B: A linear correlation was observed between ½ and ¼ serial dilutions. TGF-β1 content within the Asteoidea coelomic fluid was evaluated to be between β1 and 301 pg/ml in the tested samples.

Interference assay. The detection of TGF-β1 in spiked samples with a known concentration of standard demonstrates that there is no interference on the level of TGF-β1 detected by the kit. (Data not shown)

Conclusion: Without being bound by this hypothesis, there is a putative correlation between TGF-β1 content within the product of the present invention and its numerous effects on the human skin.

The invention claimed is:

1. A method for reducing a skin aging sign or treating a skin condition or disorder in a subject, comprising administering a composition comprising an effective amount of an Asteroidea coelomic body fluid or filtrate or concentrate thereof on the subject's skin, wherein said composition is substantially free of Asteroidea tissues or extract thereof.

2. The method of claim 1, wherein the administration results in one or more of: (a) improved epidermis cell migration; (b) increased collagen fibers thickness; (c) increased number of collagen fibers; (d) reduced keratinization of stratum corneum; (e) increased keratinocyte proliferation; (f) increased keratinocyte terminal differentiation; (g) increased epidermis thickness; (h) increased glycosaminoglycans (GAGs) expression; (i) increased density of mitotic cell in epidermis; (j) increased number of epidermis cellular layers; (k) increased expression of at least one of collagen III, collagen IV and collagen VII; (l) reduced crow's feet depth; (m) increased skin elasticity; (n) (o) reduced mouth wrinkles; (o) increased skin firmness; (p) increased cellular recolonization; and (q) increased skin moisture.

3. The method of claim 1, wherein the administration results in stimulation of the gene for a small proline-rich protein involved in cell migration.

4. The method of claim 3, wherein the small proline-rich protein is SPRR2A.

5. The method of claim 1, wherein the administration results in an increased expression of at least one of collagen III, collagen IV and collagen VII.

6. The method of claim 1, wherein the administration results in reduced crow's feet depth.

7. The method of claim 1, wherein the administration results in reduced mouth wrinkles.

8. The method of claim 1, wherein the administration results in increased skin firmness.

9. The method of claim 1, wherein the administration results in increased skin elasticity.

10. The method of claim 1, wherein the administration results in increased skin moisture.

11. The method of claim 1, wherein the administration results in increased skin cellular recolonization.

12. The method of claim 1 wherein the isolated Asteroidea coelomic body fluid filtrate or concentrate thereof is substantially free of molecules having a molecular weight below about 50 kDa.

13. The method of claim 1 wherein the isolated Asteroidea coelomic body fluid filtrate or concentrate thereof comprises is substantially free of molecules having a molecular weight about about 5 kDa.

14. The method of claim 1 wherein the isolated Asteroidea coelomic body fluid filtrate or concentrate thereof is substantially free of molecules having a molecular weight above about 5 kDa and below about 50 kDa.

15. The method of claim 1 wherein the isolated Asteroidea coelomic body fluid filtrate or concentrate thereof comprises TGF-β1.

16. The method of claim 1 wherein the isolated Asteroidea coelomic body fluid filtrate or concentrate thereof is present at a concentration between about 0.01% to about 5% w/w of the composition.

17. The method of claim 1, wherein the Asteroidea is *Asteria vulgaris*.

18. A method for reducing a skin aging sign or treating a skin condition or disorder in a subject, comprising administering a composition comprising an effective amount of an Asteroidea coelomic body fluid or filtrate or concentrate thereof on the subject's skin, wherein the isolated Asteroidea coelomic body fluid or filtrate or concentrate thereof is: (a) substantially free of molecules having a molecular weight below about 50 kDa; (b) substantially free of molecules having a molecular weight above about 5 kDa; or (c) substantially free of molecules having a molecular weight above about 50 kDa and below about 5 kDa.

19. A method for reducing a skin aging sign or a treating skin condition or disorder in a subject, comprising administering a composition comprising an effective amount of an Asteroidea coelomic body fluid or filtrate or concentrate thereof on the subject's skin, wherein the Asteroidea is *Asteria vulgaris*.

20. A method for reducing a skin aging sign or a treating skin condition or disorder in a subject, comprising administering a composition consisting of an effective amount of an Asteroidea coelomic body fluid or filtrate or concentrate thereof and one or more carriers on the subject's skin.

* * * * *